US008338566B2

(12) United States Patent
Pal et al.

(10) Patent No.: US 8,338,566 B2
(45) Date of Patent: Dec. 25, 2012

(54) **CHARACTERIZATION OF BBK07 ANTIGEN OF *BORRELIA BURGDORFERI* AND METHODS OF USE**

(75) Inventors: Utpal Pal, College Park, MD (US); Adam Steven Coleman, Crofton, MD (US)

(73) Assignee: University of Maryland, College Park Office of Technology Commercialization, College Park, MD (US)

( * ) Notice: Subject to any disclaimer, the term of this patent is extended or adjusted under 35 U.S.C. 154(b) by 134 days.

(21) Appl. No.: 12/658,929

(22) Filed: Feb. 17, 2010

(65) Prior Publication Data
US 2011/0020800 A1 Jan. 27, 2011

Related U.S. Application Data

(60) Provisional application No. 61/153,381, filed on Feb. 18, 2009.

(51) Int. Cl.
*C12Q 1/68* (2006.01)
*G01N 33/53* (2006.01)
(52) U.S. Cl. ....... 530/327; 530/350; 435/7.92; 435/6.16
(58) Field of Classification Search .................. None
See application file for complete search history.

(56) References Cited

U.S. PATENT DOCUMENTS
2005/0147999 A1* 7/2005 Choi et al. .............. 435/6

OTHER PUBLICATIONS

Ouyang, Z et al, Microbiology, 2008, vol. 154, pp. 2641-2658, Transcriptional interplay among the regulators Rrp2, RpoN and RpoS in *Borrelia burgdorferi*.*
Jewett, MW et al, Molecular Microbiology, vol. 64(5), 2007, pp. 1358-1374, The Critical role of the linear plasmid Lp36 in the infectious cycle of *Borrelia burgdorferi*.*
Brooks, Chad S. et al, Infection and Immunity, vol. 71(6), Jun. 2003, pp. 3371-3383, Global Analysis of *Borelia burgdorferi* Genes Regulated by Mammalian Host-specific Signals.*
Xu, Yaning et al, Infection and Immunity, vol. 64(9), pp. 3870-3876, Sep. 1996, Correlation of Plasmids with Infectivity of *Borrelia burgdorferi* Sensu Stricto type Strain B31.*
Barbour, Alan G et al, Infection and Immunity, vol. 76(8), pp. 3374-3389, Aug. 2008, A Genome-Wide Proteome Array Reveals a limited set of Immunogens in Natural Infections of Humans and White-Footed Mice with *Borrelia burgdorferi*.*
Gauthier, David T et al, Journal of Vet. Diagn. Invest., vol. 11, pp. 259-265, 1999, Western immunoblot analysis for distinguishing vaccination and infection status with *Borrelia burgdorferi* (Lyme disease) in dogs.*
Coleman, Adam S. et al, Clinical and Vaccine Immunology, vol. 16(11), pp. 1569-1575, Nov. 2009, BBK07, a Dominant In Vivo antigen of *Borrelia burgdorferi*, Is a Potential Marker for Serodiagnosis of Lyme Disease, published on line Sep. 2009.*

* cited by examiner

*Primary Examiner* — Albert Navarro
*Assistant Examiner* — Ginny Portner
(74) *Attorney, Agent, or Firm* — Pratt & Associates, Inc.; Sana A. Pratt

(57) ABSTRACT

In this application is described the characterization *Borrelia burgdorferi* lipoprotein BBK07, an in vivo expressed and surface-exposed immunogen. BBK07 expression in the infected hose can be detected at the RNA and protein level as early as the first week of infection. Therefore, described is the use of BBK07 antigen and immunogenic epitopes as well as bbk07 nucleotides in methods and kits for the diagnosis of Lyme disease.

28 Claims, 7 Drawing Sheets

Figure 2
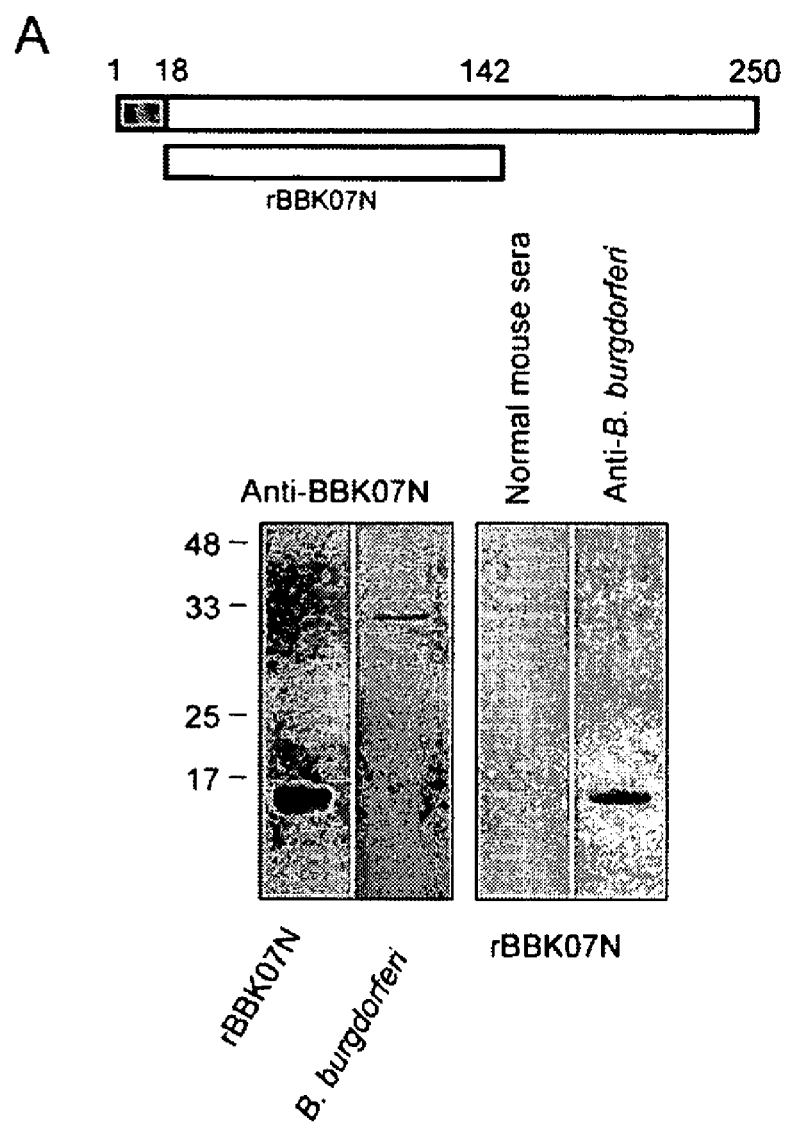
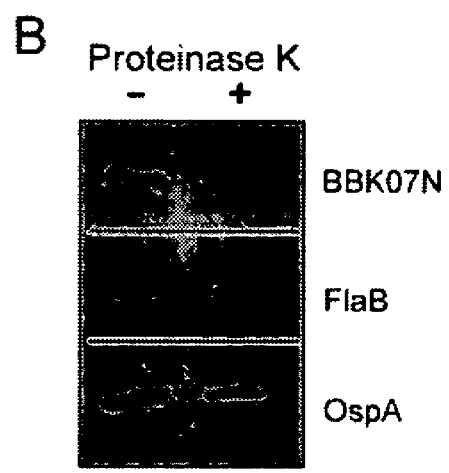

Figure 6
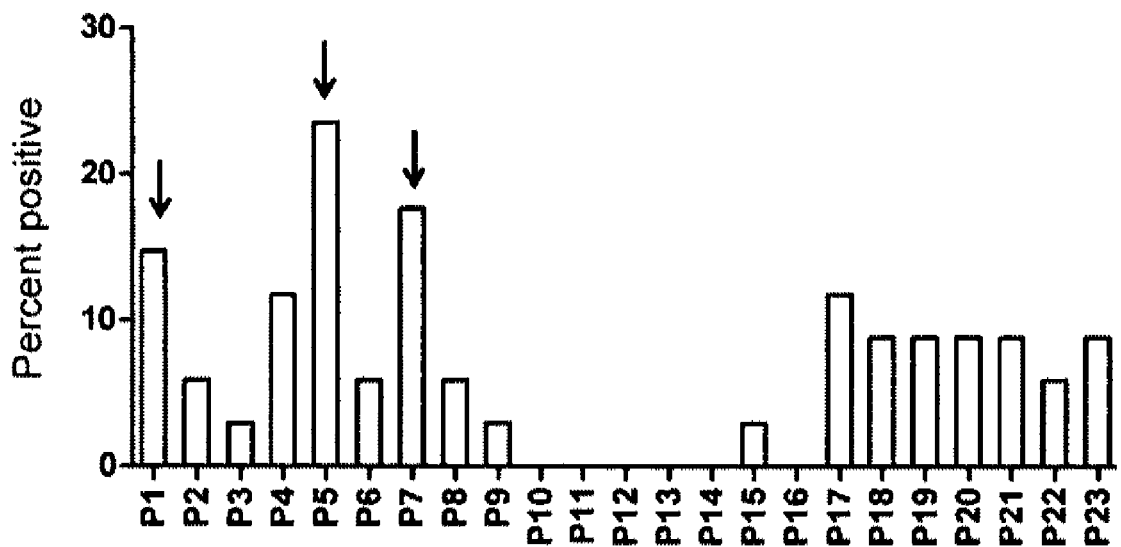
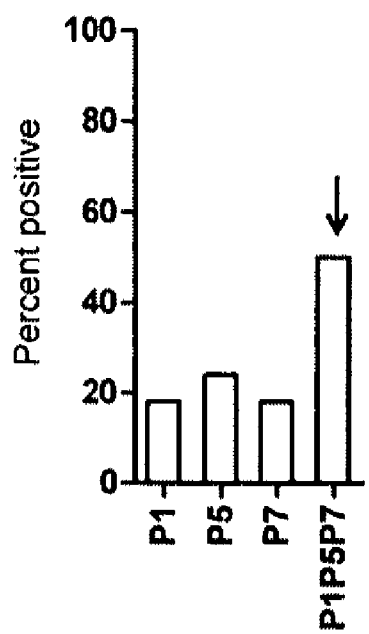

SEQUENCE LISTING

<160> NUMBER OF SEQ ID NOS: 35

<210> SEQ ID NO 1
<211> LENGTH: 250
<212> TYPE: PRT
<213> ORGANISM: Borrelia burgdorferi
<220> FEATURE:
<223> OTHER INFORMATION: isolate B31 BBK07

<400> SEQUENCE: 1

Met Ser Lys Leu Ile Leu Ala Ile Ser Ile
                 5                  10

Leu Leu Ile Ile Ser Cys Lys Trp His Val
                15                  20

Asp Asn Pro Ile Asp Glu Ala Thr Ala Glu
                25                  30

Ser Lys Ser Ala Leu Thr Ser Val Asp Gln
                35                  40

Val Leu Asp Glu Ile Ser Glu Ala Thr Gly
                45                  50

Leu Ser Ser Glu Lys Ile Thr Lys Leu Thr
                55                  60

Pro Glu Glu Leu Glu Asn Leu Ala Lys Glu
                65                  70

Ala Gln Asp Asp Ser Glu Lys Ser Lys Lys
                75                  80

Glu Ile Glu Asp Gln Lys Asn Thr Lys Glu
                85                  90

Ser Lys Asn Ile Glu Val Lys Asp Thr Pro
                95                 100

Arg Leu Ile Lys Leu Ile Lys Asn Ser Ser
               105                 110

Glu Lys Ile Asp Ser Val Phe Gln Thr Leu
               115                 120

Ile Asn Ile Gly Tyr Asn Arg Thr Tyr Arg
               125                 130

Arg Lys Ser Asn Leu Lys Asn Gly Leu Lys
               135                 140

Met Val Lys Leu Leu Asp Glu Leu Leu Lys
               145                 150

Ile Ser Val Ser Ser Asn Gly Asp Lys Ser
               155                 160

Thr Gln Lys Tyr Asn Glu Leu Lys Thr Val
               165                 170

Val Asn Arg Phe Asn Ala Glu Asn Ser Ala
               175                 180

Ile Lys Val Pro Leu Glu Asn Gly Ser Lys
               185                 190

Ile Glu Ala Lys Lys Cys Ile Lys Thr Leu
               195                 200

Met Thr Asn Val Glu Thr Tyr Phe Lys Gly
               205                 210

Val Ser Thr Glu Leu Lys Asp Lys Lys Asp
               215                 220

```
Asp Lys Tyr Thr Lys Ile Leu Ala Ala Leu
            225                 230

Ser Glu Ala Ala Asn Lys Ile Glu Asn Ala
            235                 240

Ala Met Ala Ile His Leu Cys Phe Asn Asn
            245                 250

<210> SEQ ID NO 2
<211> LENGTH: 14
<212> TYPE: PRT
<213> ORGANISM: Artificial sequence
<220> FEATURE:
<223> OTHER INFORMATION: isolate B31 BBK07 linear peptide

<400> SEQUENCE: 2

Cys Lys Trp His Val Asp Asn Pro Ile
              5                 10

Asp Glu Ala Thr Ala

<210> SEQ ID NO 3
<211> LENGTH: 14
<212> TYPE: PRT
<213> ORGANISM: Artificial sequence
<220> FEATURE:
<223> OTHER INFORMATION: isolate B31 BBK07 linear peptide

<400> SEQUENCE: 3

Ile Thr Lys Leu Thr Pro Glu Glu Leu Glu
              5                 10

Asn Leu Ala Lys

<210> SEQ ID NO 4
<211> LENGTH: 14
<212> TYPE: PRT
<213> ORGANISM: Artificial sequence
<220> FEATURE:
<223> OTHER INFORMATION: isolate B31 linear peptide

<400> SEQUENCE: 4

Glu Lys Ser Lys Lys Glu Ile Glu Asp Gln
              5                 10

Lys Asn Thr Lys

<210> SEQ ID NO 5
<211> LENGTH: 20
<212> TYPE: DNA
<213> ORGANISM: Artificial Sequence
<220> FEATURE:
<223> OTHER INFORMATION: forward primer

<400> SEQUENCE: 5
cctatttcaa gggcgtgagc                                                20

<210> SEQ ID NO 6
<211> LENGTH: 20
<212> TYPE: DNA
<213> ORGANISM: Artificial Sequence
<220> FEATURE:
<223> OTHER INFORMATION: reverse primer

<400> SEQUENCE: 6
tatggccatt gctgcattct                                                20

<210> SEQ ID NO 7
```

<211> LENGTH: 753
<212> TYPE: DNA
<213> ORGANISM: Borrelia burgdorferi
<220> FEATURE:
<223> OTHER INFORMATION: isolate B31 BBK07

<400> SEQUENCE: 7

| | |
|---|---|
| atgagtaaac taatattggc aatatctata ctgctaataa | 40 |
| tttcatgtaa atggcatgta gacaatccca ttgatgaagc | 80 |
| aactgcagaa agtaaatcag cactaacatc tgttgatcaa | 120 |
| gtattagatg agataagtga agctacaggt ctaagttcgg | 160 |
| aaaaaatcac aaaattaact ccggaagagc tagaaaattt | 200 |
| agcaaaggaa gctcaagatg attctgaaaa atccaaaaaa | 240 |
| gaaattgaag atcaaaaaaa taccaaggaa agtaaaaaca | 280 |
| tagaagtaaa ggatactcct cgcttaatca aattgattaa | 320 |
| gaattcatca gaaaaaattg attcggtttt tcaaacacta | 360 |
| attaatatag gttataatgc tacctatgca gccaaaagta | 400 |
| atttgaagaa tggactaaag atggtgaaat tactggatga | 440 |
| gttgctaaaa atatcggtaa gtagcaatgg tgataaaagt | 480 |
| acccaaaaat acaatgaact taaaaccgtt gtaaataggt | 520 |
| ttaatgctga aaattcagcg ataaaggtac cattagaaaa | 560 |
| tggtagtaaa attgaagcca aaagtgcat aaaaactctt | 600 |
| atgaccaatg tggaaaccta tttcaagggc gtgagcaccg | 640 |
| aactcaaaga taaaaaagac gacaaatata ctaaaatatt | 680 |
| ggcagctttg agtgaggcag ccaataaaat agagaatgca | 720 |
| gcaatggcca tacatttgtg ctttaataat taa | 753 |

<210> SEQ ID NO 8
<211> LENGTH: 10
<212> TYPE: PRT
<213> ORGANISM: Artificial sequence
<220> FEATURE:
<223> OTHER INFORMATION: Borrelia burgdorferi OspC linear epitope

<400> SEQUENCE: 8

Pro Val Val Ala Glu Ser Pro Lys Lys Pro
              5                  10

<210> SEQ ID NO 9
<211> LENGTH: 14
<212> TYPE: PRT
<213> ORGANISM: Artificial sequence
<220> FEATURE:
<223> OTHER INFORMATION: Borrelia burgdorferi OspC linear epitope

<400> SEQUENCE: 9

Ile Leu Met Thr Leu Phe Leu Phe Ile Ser
              5                  10

Cys Asn Asn Ser

<210> SEQ ID NO 10
<211> LENGTH: 33
<212> TYPE: DNA
<213> ORGANISM: Artificial Sequence
<220> FEATURE:

<223> OTHER INFORMATION: forward primer

<400> SEQUENCE: 10
aatctagaat gtggcatgta gacaatccca ttg                33

<210> SEQ ID NO 11
<211> LENGTH: 31
<212> TYPE: DNA
<213> ORGANISM: Artificial Sequence
<220> FEATURE:
<223> OTHER INFORMATION: reverse primer

<400> SEQUENCE: 11
ccgggatcca ttacatcttt agtccattct t                31

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
ttcaatcagg taactgcaca                20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gacgcttgag accctgaaag                20

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
gctgaaaatt cggtaagcgt tt                22

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
taagttcgct gcatacacct tca                23

<210> SEQ ID NO 16
<211> LENGTH: 14
<212> TYPE: PRT
<213> ORGANISM: Artificial sequence
<220> FEATURE:
<223> OTHER INFORMATION: Borrelia burgdorferi isolate B31linear peptide

<400> SEQUENCE: 16

Glu Ala Thr Ala Glu Ser Lys Ser Ala Leu
                5                   10

Thr Ser Val Asp

<210> SEQ ID NO 17
<211> LENGTH: 14
<212> TYPE: PRT
<213> ORGANISM: Artificial Sequence
<220> FEATURE:
<223> OTHER INFORMATION: Borrelia burgdorferi isolate B31linear peptide

<400> SEQUENCE: 17

Thr Ser Val Asp Gln Val Leu Asp Glu Ile
                5                   10
Ser Glu Ala Thr

<210> SEQ ID NO 18
<211> LENGTH: 14
<212> TYPE: PRT
<213> ORGANISM: Artificial sequence
<220> FEATURE:
<223> OTHER INFORMATION: Borrelia burgdorferi isolate B31linear peptide

<400> SEQUENCE: 18

Ser Glu Ala Thr Gly Leu Ser Ser Glu Lys
                5                   10
Ile Thr Lys Leu

<210> SEQ ID NO 19
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 19

Asn Leu Ala Lys Glu Ala Gln Asp Asp Ser
                5                   10
Glu Lys Ser Lys

<210> SEQ ID NO 20
<211> LENGTH: 14
<212> TYPE: PRT
<213> ORGANISM: Artificial sequence
<220> FEATURE:
<223> OTHER INFORMATION: Borrelia burgdorferi isolate B31Linear peptide

<400> SEQUENCE: 20

Lys Asn Thr Lys Glu Ser Lys Asn Ile Glu
                5                   10
Val Lys Asp Thr

<210> SEQ ID NO 21
<211> LENGTH: 14
<212> TYPE: PRT
<213> ORGANISM: Artificial sequence
<220> FEATURE:
<223> OTHER INFORMATION: Borrelia burgdorferi isolate B31linear peptide

<400> SEQUENCE: 21

Val Lys Asp Thr Pro Arg Leu Ile Lys Leu
                5                   10
Ile Lys Asn Ser

<210> SEQ ID NO 22
<211> LENGTH: 14
<212> TYPE: PRT

<213> ORGANISM: Artificial sequence
<220> FEATURE:
<223> OTHER INFORMATION: Borrelia burgdorferi isolate B31 linear peptide

<400> SEQUENCE: 22

Ile Lys Asn Ser Ser Glu Lys Ile Asp Ser
                 5                  10
Val Phe Gln Thr

<210> SEQ ID NO 23
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 23

Val Phe Gln Thr Leu Ile Asn Ile Gly Tyr
                 5                  10
Asn Ala Thr Tyr

<210> SEQ ID NO 24
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 24

Asn Ala Thr Tyr Ala Ala Lys Ser Asn Leu
                 5                  10
Lys Asn Gly Leu

<210> SEQ ID NO 25
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 25

Lys Asn Gly Leu Lys Met Val Lys Leu Leu
                 5                  10
Asp Glu Leu Leu

<210> SEQ ID NO 26
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 26

Asp Glu Leu Leu Lys Ile Ser Val Ser Ser
                 5                  10
Asn Gly Asp Lys

<210> SEQ ID NO 27
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 27

Asn Gly Asp Lys Ser Thr Gln Lys Tyr Asn
                5                   10

Glu Leu Lys Thr

<210> SEQ ID NO 28
<211> LENGTH: 13
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 28

Glu Leu Lys Thr Trp Asn Arg Phe Asn Ala
                5                   10

Glu Asn Ser

<210> SEQ ID NO 29
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 29

Ala Glu Asn Ser Ala Ile Lys Val Pro Leu
                5                   10

Glu Asn Gly Ser

<210> SEQ ID NO 30
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 30

Glu Asn Gly Ser Lys Ile Glu Ala Lys Lys
                5                   10

Cys Ile Lys Thr

<210> SEQ ID NO 31
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 31

Cys Ile Lys Thr Leu Met Thr Asn Val Glu
                5                   10

Thr Tyr Phe Lys

<210> SEQ ID NO 32
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 32

Thr Tyr Phe Lys Gly Val Ser Thr Glu Leu
                5                   10

Lys Asp Lys Lys

```
<210> SEQ ID NO 33
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 33

Lys Asp Lys Lys Asp Asp Lys Tyr Thr Lys
                 5                  10

Ile Leu Ala Ala

<210> SEQ ID NO 34
<211> LENGTH: 14
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 34

Ile Leu Ala Ala Leu Ser Glu Ala Ala Asn
                 5                  10

Lys Ile Glu Asn

<210> SEQ ID NO 35
<211> LENGTH: 15
<212> TYPE: PRT
<213> ORGANISM: Artificial sequence
<220> FEATURE:
<223> OTHER INFORMATION: Borrelia burgdorferi isolate B31 linear peptide

<400> SEQUENCE: 35

Lys Ile Glu Asn Ala Ala Met Ala Ile His
                 5                  10

Leu Cys Phe Asn Asn
                15
```

CHARACTERIZATION OF BBK07 ANTIGEN OF *BORRELIA BURGDORFERI* AND METHODS OF USE

This application claims the benefit of priority from Provisional Application Ser. No. 61/153,381 filed on Feb. 18, 2009.

STATEMENT OF FEDERALLY SPONSORED RESEARCH AND DEVELOPMENT

This invention was made with government support under Public Health Service grants AR055323 and AI080615 from the National Institutes of Health. The US Government has certain rights in the invention.

INTRODUCTION

Since the identification of *Borrelia burgdorferi* as the causative agent of Lyme disease (LD) over 25 years ago the number of reported cases of LD has increased steadily (Bacon et al., 2008, MMWR Surveill. Summ. 57, 1-9; Steere A. C. et al., 1977, Athritis Rheum. 20, 7-17; Steere, A. C. et al., 2004, J. Clin. Invest. 113, 1093; Piesman and Eisen, 2008, Annu. REb. Entomol. 2008, 53, 323-343). In some United States counties the incidence is more than 500 cases per 100,000 individuals, and more than 20,000 cases in the United States are diagnosed each year (Bacon et al., 2008, supra). Difficulties in diagnosis have long complicated the treatment of LD, as the bite of an infected tick may go unnoticed by the patient, and the clinical manifestations of LD can significantly vary amongst diagnosed patients (Steere, A. C. 2004, J. Clin. Invest. 113, 1093-1101). Common symptoms such as fever, malaise, and arthritis can resemble those caused by other conditions, further complicating diagnosis. Antibiotic therapy is highly effective, especially if administered in the early stages of LD, however, serious complications can result from false diagnoses and inappropriate treatment (Brown S. L. et al., 1999, J. Am. Med. Assoc. 281, 62-66; Ettestad, P. J. et al. 1995, J. Infect. Dis. 171, 356-361; Patel, R. et al., 2003, J. Neurol. 250, 1318-1327; Steere, A. C. et al. 1984, Yale J. Biol. Med. 57, 557-560; Tugwell, P. et al., 1997, Ann. Intern. Med. 127, 1109-1123). There is no commercially available vaccine for human LD, so the development of accurate, sensitive laboratory diagnosis is an important goal of LD research.

While many laboratory methods have been used to assess *B. burgdorferi* infection, direct detection of the bacterium is difficult due to the low pathogen load in clinical samples (Aguero-Rosenfeld, M. E. et al., 1993, J. Clin. Microbiol. 31, 3090-3095; Johnston, Y. E. et al., 1985, Am. J. patho. 118, 26-34). Likewise, the extremely slow growth of *B. burgdorferi*, the high cost and the labor-intensive procedure needed to culture this bacterium have limited the effectiveness of culture as a diagnostic tool (Nadelman and Wormser, 1998, Lancet 352, 557-565; Stanek and Strle, 2003, Lancet 362, 1639-1647). PCR detection is possible (Schwartz, I. et al., 1992, J. Clin. Microbiol. 30, 3082-3088), but not widely used for diagnosis, due primarily to low sensitivity in tissues, such as cerebrospinal fluid and blood (Aguero-Rosenfeld et al., 1993, supra). Instead, the primary means used to detect *B. burgdorferi* exposure is serodiagnosis (Aguero-Rosenfeld et al., 1993, supra). Immunodetection has been performed using whole cell antigens, as well as recombinant proteins or peptide fragments (Aguero-Rosenfeld et al., 1993, supra). Whole cell lysate provides a wide variety of antigens for detection, but is difficult to standardize due to variations in protein expression by culture growth phase (Ramamoorthy and Philipp, 1998, Infect. Immun. 66, 5119-5124). False positive results are also an issue, as antibodies against other bacteria can cross-react with conserved *B. burgdorferi* proteins (Barbour, A. G. et al., 1986, Infect. Immun. 52, 439-554; Dressler, F. et al., 1993, J. Infect. Dis. 167, 392-400; Hansen, K. et al., 1988, Infect. Immun. 56, 2047-2053; Ma, B. et al., 1992, J. Clin. Microbiol. 30, 370-376).

To reduce cross-reactivity, several recombinant *B. burgdorferi* antigens and various fragments thereof have been evaluated as serodiagnostic markers for LD, including OspC (Padula, S. J. et al., 1994, J. Clin. Microbiol. 32, 1733-1738), BmpA (Simpson, W. J. et al., 1990, J. Clin. Microbiol. 28, 1329-1337), VlsE (Lawrenz, M. B. et al., 1999, J. Clin. Microbiol. 37, 3997-4004), BBK32 (Heikkila, T. et al., 2002, J. Clin. Microbiol. 40, 1174-1180), L25 (Mueller, M. et al., 2006, J. Clin. Microbiol. 44, 3778-3780), P37 (Magnarelli, L. A. et al, 2000, J. Clin. Microbiol. 38, 1735-1739) and DbpA (Goettner, G. et al., 2005, J. Clin. Microbiol. 43, 3602-3609). OspC is exposed on the *B. burgdorferi* surface, is produced during early infection, and is highly immunogenic (Aguero-Rosenfeld, M. E. et al., 1993, J. Clin. Microbiol. 31, 3090-3095; Dressler, F. et al., 1993, J. Infect. Dis. 167, 392-400; Engstrom, S. M. et al., 1995, J. Clin. Microbiol. 33, 419-427; Padula, S. J. et al., 1994, supra). A peptide fragment termed pepCIO, containing a conserved immunogenic epitope, has been developed for serodiagnosis (Mueller, M. J. et al., 2006, supra). BmpA, another surface-exposed protein, has also been studied for use in diagnosis (Bryksin, A. V. et al., 2005, Clin. Diagn. Lab. Immunol. 12, 935-940; Simpson, W. J. et al., 1990, supra). Though immunogenic, significant protein sequence heterogeneity exists among *B. burgdorferi* isolates, constituting several serotypes, which limit the effectiveness of both OspC (Earnhart, C. G. et al., 2005, Infect. Immun. 73, 7869-7877) and BmpA as serodiagnostic markers (Roessler, D. et al., 1997, J. Clin. Microbiol. 35, 2757-2758). VlsE is a dominant surface-exposed antigen of *B. burgdorferi*, a lipoprotein that undergoes antigenic variation by genetic recombination with silent vis cassettes (Zhang, J. R. et al., 1997, Cell 89, 275-285). Expressed throughout late infection, VlsE and C6, a conserved peptide fragment of VlsE, have been evaluated as serodiagnostic markers for LD (Embers, M. E. et al., 2007, Clin. Vaccine Immunol. 14, 90-93; Lawrenz, M. B. et al., 1999, J. Clin. Microbiol. 37, 3997-4004; Liang, F. T. et al., 2000, J. Infect. Dis. 182, 1455-1462). These studies suggest that while the use of recombinant proteins can reduce cross-reactivity, thereby enhancing specificity, the use of only select antigens can reduce the sensitivity of the diagnostic test (Magnarelli, L A. et al., 1996, J. Clin. Microbiol. 38, 1735-1739). A promising sensitivity in such tests was reported by Bacon et al. (Bacon, R. M. et al., 2003, J. Infect. Dis. 187, 1187-1199). Using kinetic ELISA, the combined detection of IgM against pepC10 and IgG against C6 provided 78% sensitivity in all tested samples. While assays using only recombinant antigens show promise, the identification and inclusion of more immunodominant antigens could improve the sensitivity of these tests.

In an effort to more completely catalogue antigens produced during infection, a recent study by Barbour et al. used synthetic protein arrays to test the immunogenicity of the majority of *B. burgdorferi* open reading frames (Barbour, A. G. et al., 2008, Infect. Immun. 76, 3374-3389). Though most open reading frames were not measurably immunogenic, they identified several novel antigens, including BBK07 and BBK12, putative lipoproteins from the linear plasmid 1p36. These proteins are extremely similar in sequence, though BBK07 is slightly larger than BBK12 (250 and 232 amino acids, respectively) (Fraser, C. M. et al., 1997, Nature 390, 580-586). The genes are members of paralogous family 59, and are 87% identical in their overlapping amino acid sequences. While both BBK07 and BBK12 were identified as immunogens and potential antigenic markers, a detailed characterization of their expression and the resulting immune response was not explored. We sought to characterize the expression, surface localization and immune response against BBK07 to further evaluate its inclusion as a diagnostic marker to improve the accuracy and sensitivity of LD serodiagnosis.

SUMMARY OF THE INVENTION

In this application is described the characterization of a recently identified *Borrelia burgdorferi* immunogen, BBK07. Expression of the immunogen in the spirochete infection cycle and its potential for use as a serodiagnostic marker for Lyme disease is evaluated.

A total of 100 spirochete genes were selected for expression analysis, based on their putative association with the spirochete membrane, as determined by their database annotation and in silico analysis for extracellular exposure. The expression of each gene in different murine tissues was analyzed, and bbk07 was chosen as the focus of study through a consideration of the detailed expression patterns of the gene during the genesis of murine disease, immunogenicity, surface exposure, sequence conservation and published information.

The inventors have now characterized the expression of BBK07, both at the RNA level and the protein level, its surface localization and the immune response generated against this antigen.

Transcription of bbk07 was not detectable in any tested stages of ticks. The inventors show that bbk07 is expressed at extremely low levels in vitro and in ticks, but is dramatically induced by spirochetes once introduced into the host, and is highly expressed throughout mammalian infection preceding the development of disease, between day 5 and 10 of infection. In contrast, the expression of bbk12, a paralog of bbk07 with 87% amino acid identity, although expressed in vitro, remained undetectable in vivo throughout murine infection and in ticks.

The inventors discovered that BBK07 is expressed only in the infected host during the first 4 weeks of infection. Furthermore, BBK07 antigen is localized in the outer membrane and the amino-terminal domain of the antigen is exposed on the microbial surface. A truncated BBK07 protein representing the amino-terminal domain is able to effectively detect antibodies to *B. burgdorferi*, both in experimentally infected mice and in humans.

Therefore, the present invention provides a *B. burgdorferi* nucleotide sequence for detecting the expression of the gene at the RNA level. The *B. burgdorferi* genomic sequence was reported by Fraser, C. M. et al., 1997 (Nature 390, 580-586) and by Casjens, S. et al., 2000 (Mol. Microbiol. 35, 490-516) and has been deposited in GenBank at accession no. AAC66153. The nucleotide sequence can be used to design probes and primer sequences in order to detect expression of the gene during the early stages of infection or contraction of Lyme disease and can be used in an assay and kit for diagnosis Lyme disease.

In one aspect, the bbk07 gene expression can be detected using quantitative reverse transcription polymerase chain reaction using primers designed to specifically amplify the target gene. Therefore, a method for detecting and measuring RNA expression of *B. burgdorferi* is provided. Also included in the invention are primer sets capable of priming amplification of the bbk07 DNA sequences; kits containing primer sets for determining the quantity of expression of bbk07; kits for the detection of *B. burgdorferi* nucleic acids in a sample, the kits containing one or more nucleic acid probe specific for the bbk07 sequences, together with a means for detecting a specific hybridization with the probe.

In another aspect, BBK07-specific immune response during active borrelial infection can be detected in the infected host. Therefore, a method for detecting BBK07 antibody in a biological sample from a subject suspected of having Lyme disease is provided.

In one specific embodiment, a recombinant protein fragment BBK07N, containing the amino terminal part of the BBK07 protein and excluding the signal peptide, amino acids 18-142. The complete predicted amino acid sequence of BBK07 of *B. burgdorferi* isolate B31 is shown in SEQ ID NO:1, is used. The recombinant protein is able to detect specific antibodies present in biological samples from an infected host. The anti-BBK07 immune reaction is detectable one week after infection by *B. burgdorferi* and remains elevated throughout the infection.

Additionally, the inventors have tested 23 linear peptide epitopes from BBK07 and identified 3 amino-terminal BBK07 peptides (Peptide no. 1-C K W H V D N P I D E A T A (SEQ ID NO:2), Peptide no. 5-I T K L T P E E L E N L A K (SEQ ID NO:3) and Peptide no. 7-E K S K K E I E D Q K N T K, SEQ ID NO:4) that contain the most immunogenic epitopes, which enhance the detection sensitivity of Lyme disease. Peptide no. 5 housed the most immunogenic epitope amongst all 23 peptides tested. However, use of a combination of 3 above-mentioned immunodominant peptides (P1+P5+P7) displayed the most superior serodiagnostic potential in the ELISA assay. The peptide combination (P1+P5+P7) enhanced the serodiagnosis sensitivity of the assay up to 50% (17 out of 34 positive for Lyme disease), when compared to ones using individual peptides.

Therefore, in another aspect, the invention provides a method and kit for detecting *B. burgdorferi* infection in a subject, the method comprising detecting BBK07 antibodies in a biological sample from the subject using any immunogenic peptides, for example, Peptide no. 1, Peptide no. 5, or Peptide no. 7, alone or in any combination. Kits for detection of antibodies against the BBK07 antigen of *B. burgdorferi* and kits containing one or more BBK07 immunogenic peptide, recombinant polypeptide, or BBK07 protein, together with means for detecting a specific binding of antibodies to the BBK07 peptide are part of the invention.

In yet another embodiment, the present invention provides a diagnostic assay for the early detection of borrelial infection, the assay comprising contacting a biological sample from a subject suspected of having Lyme disease with one or a combination of two or more BBK07 protein, BBK07N protein, an immunogenic peptide or polypeptide, capable of forming a complex with anti-BBK07 antibodies found in the sample, and measuring the presence or absence of the complex, wherein presence of the complex confirms the presence of the infection and absence of the complex denies the presence of the infection.

Interestingly, the assay described is able to differentiate between an immune response to active infection and an immune response generated as a result of vaccination with lysed spirochetes. In fact, the recombinant antigen BBK07N proved to be more sensitive than several antigens currently used in Lyme disease diagnosis.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

(B) bbk07 expression pattern in vivo. The transcriptional profile of bbk07 throughout representative stages of the life cycle of *B. burgdorferi* was measured by qRT-PCR. Mice (3 mice per time point) and ticks (3 ticks per time point) were infected with *B. burgdorferi*. Total RNA was isolated from infected tissues representing the complete life cycle of *B. burgdorferi*: fed nymphs, infected murine tissues collected at weekly intervals through four weeks after infection, feeding larva, and unfed nymphs. bbk07 was expressed in all murine tissues tested but was undetectable in tick samples. All qRT-PCR results represent the mean and SEM of four qPCR measurements from two independent infection experiments.

FIG. 2. Amino terminal part of BBK07 is surface exposed and immunogenic.

(A) Upper panel represents the schematic of BBK07 showing location of recombinant amino-terminal BBK07 protein fragment used in the current study. A protein fragment lacking the putative signal peptide (grey box) starting from amino-terminal to half of the protein length was purified, and termed BBK07N. Generated mouse anti-BBK07N sera recognizes recombinant truncated protein and native BBK07 (bottom left two panels), while recombinant BBK07N detects BBK07-specific antibody in infected mouse serum two weeks after infection (bottom right two panels). Mice were immunized with BBK07N in order to generate BBK07N antiserum. The resulting serum was used to probe 100 ng of purified BBK07N and 1 ug of *B. burgdorferi* cell lysate.

(B) Surface exposure of BBK07. Viable *B. burgdorferi* cells were incubated with (+) or without (−) Proteinase K and subjected to immunoblotting using antiserum against BBK07N, FlaB and OspA. FlaB and OspA were used as subsurface and surface controls, respectively. While the levels of FlaB did not significantly decrease, both OspA and BBK07 showed significant degradation in the presence of Proteinase K.

Figure 3:
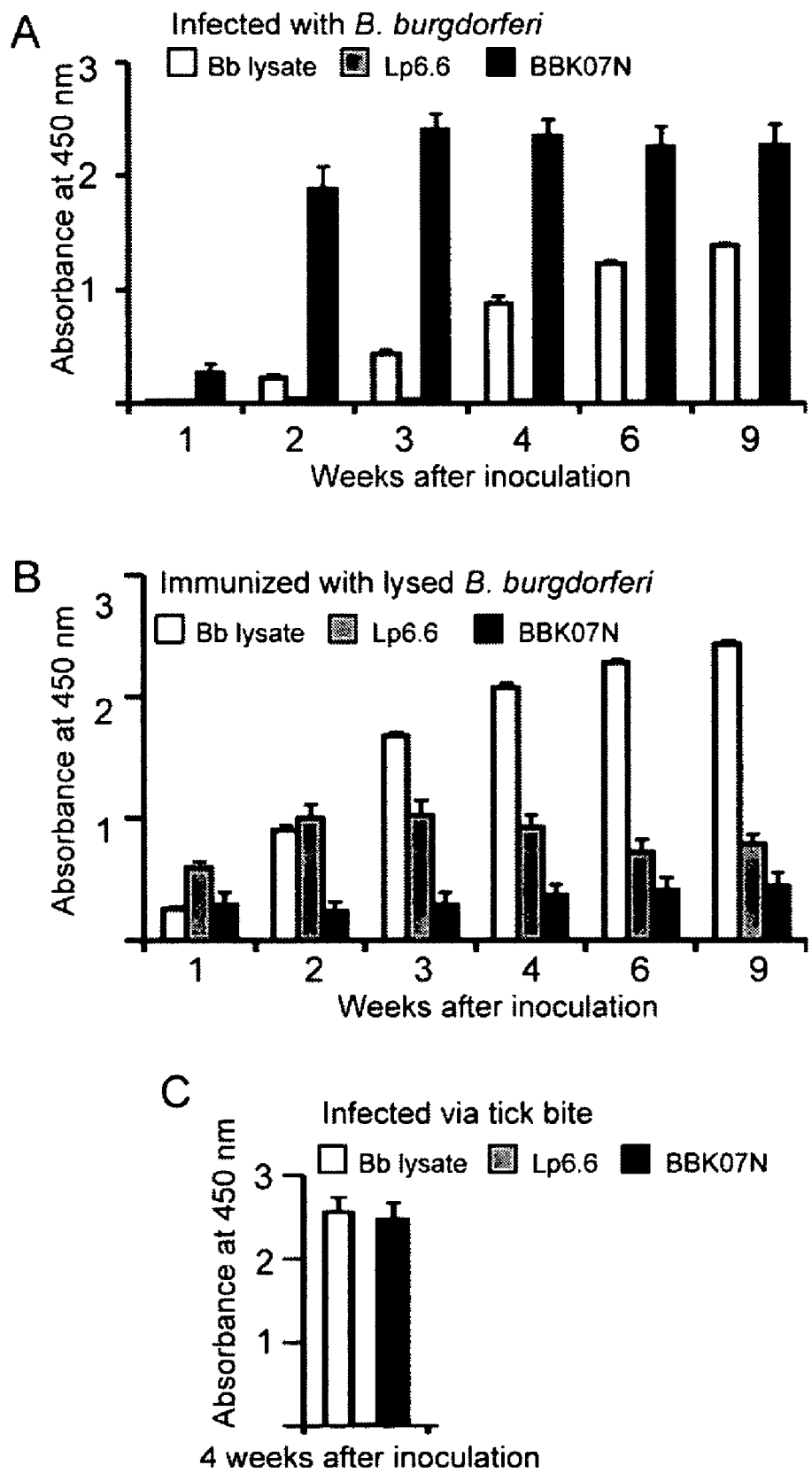

FIG. 3. BBK07-specific antibody develops early during infection but is absent in hosts immunized with lysed pathogens.

(A) BBK07 antibodies are detectable during early infection. Serum samples from mice needle-inoculated with *B. burgdorferi* were collected at several time points after infection. The immune response to *B. burgdorferi* lysate, and purified Lp6.6 and BBK07N proteins was measured by ELISA.

(B) Mice immunized with sonicated *B. burgdorferi* generate an insignificant immune response against BBK07. Mice were immunized weekly with *B. burgdorferi* lysate and serum samples were tested by ELISA as described in A.

(C) BBK07 antibodies present during natural tick-borne infection of mice. Mice were infected by tick bite, and serum samples tested by ELISA. The immune response was similar to that of the needle-infected mice. The bars represent the mean and SEM of duplicate measurements of two experiments.

Figure 4:
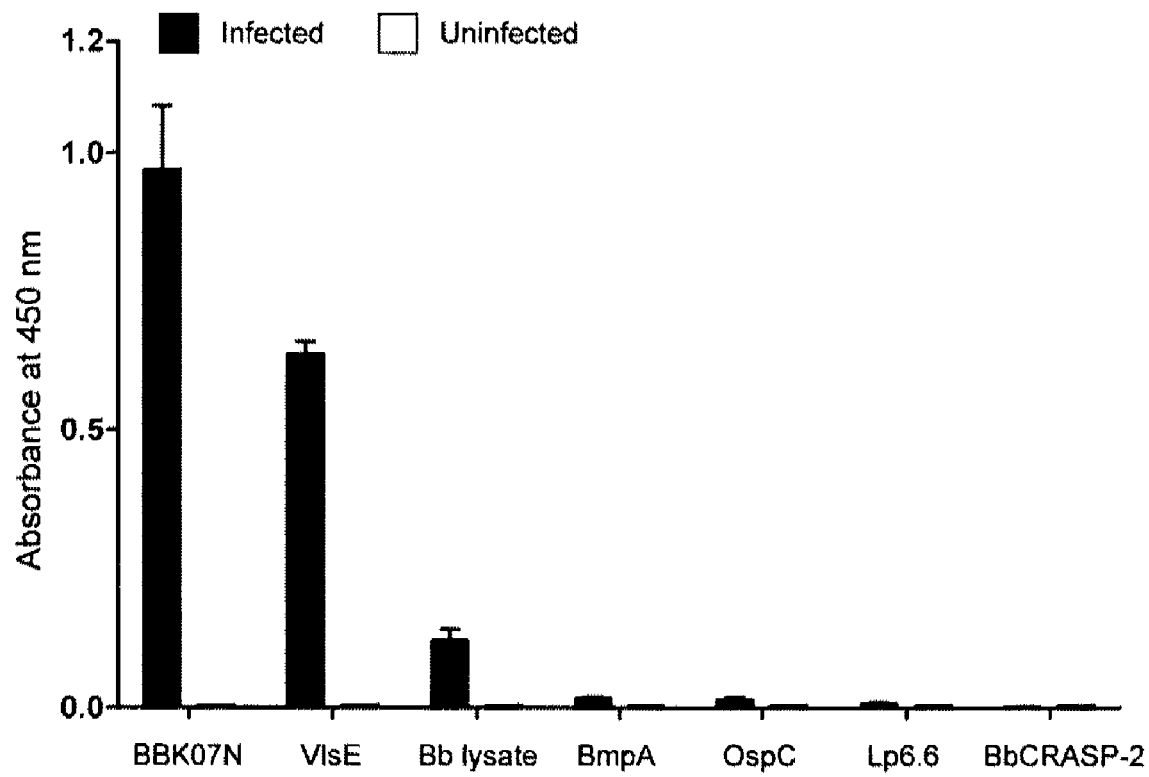

FIG. 4. Comparative immunogenicity of BBK07 against other antigens in mice. Pooled sera from groups of two-week post-infection (black bars) and uninfected (white bars) mice were used to probe 100 ng of purified proteins or sonicated *B. burgdorferi* lysate and the levels of specific antibody responses were measured by ELISA. Naive mouse sera had low reactivity to all antigens. As wells containing BBK07N and VlsE quickly reached the upper detection limit of the assay, the reaction was stopped 1 minute after the addition of the chromogenic substrate. The bars represent the mean and SEM from duplicate measurements of two independent mouse experiments. Except for VlsE, differences in antibody responses against BBK07N are significantly higher than other antigens (*$P<0.05$).

Figure 5:
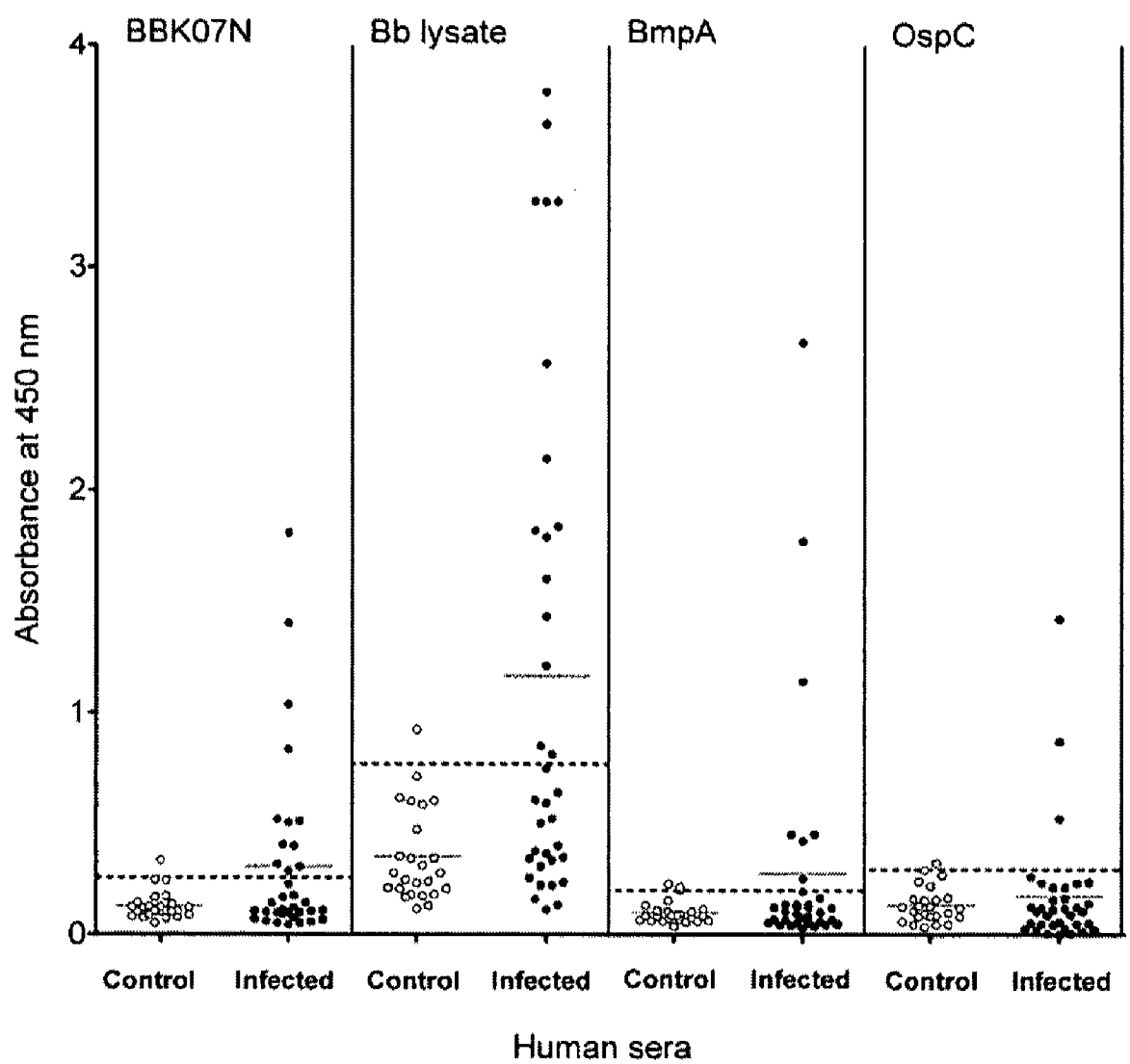

FIG. 5. BBK07N as a potential antigenic target for serodiagnosis of human Lyme disease. Human sera from healthy individuals (white circles, n=25) and individuals infected with Lyme disease (black circles, n=35) were used to probe 100 ng of purified proteins or sonicated *B. burgdorferi* lysate by ELISA. The mean value of each group is indicated by a horizontal gray line. The cutoff value of each antigen (horizontal dotted line) was defined as the absorbance value of the $95^{th}$ percentile of the uninfected sera. Serum with a value greater than the cutoff value was considered a positive result.

FIG. 6. Comparative serodiagnostic potential of twenty-three overlapping BBK07 peptides. A, A peptide library consisting of twenty-three overlapping BBK07 was screened for immunodominant epitopes by an assessment of their reactivity in sera from patients diagnosed with LD or from healthy donors. Bars represent the percentage of diagnosed serum samples above the cutoff value, as tested once. Selected amino-terminal peptides (P1, P5 and P7, marked by arrows) displayed highest immunogenicity. B, A combination of selected peptides further enhances serodiagnostic potential. Peptides P1, P5, P7, and all 3 peptides combined were tested in three independent ELISA experiments for reactivity with human serum. Serum samples were considered positive if above the cutoff value in at least 2 out of 3 experiments. A combination of peptides P1, P5, and P7 (marked by arrow) enhanced the sensitivity indicating superior serodiagnostic potential than that with individual peptides.

Figure 7:
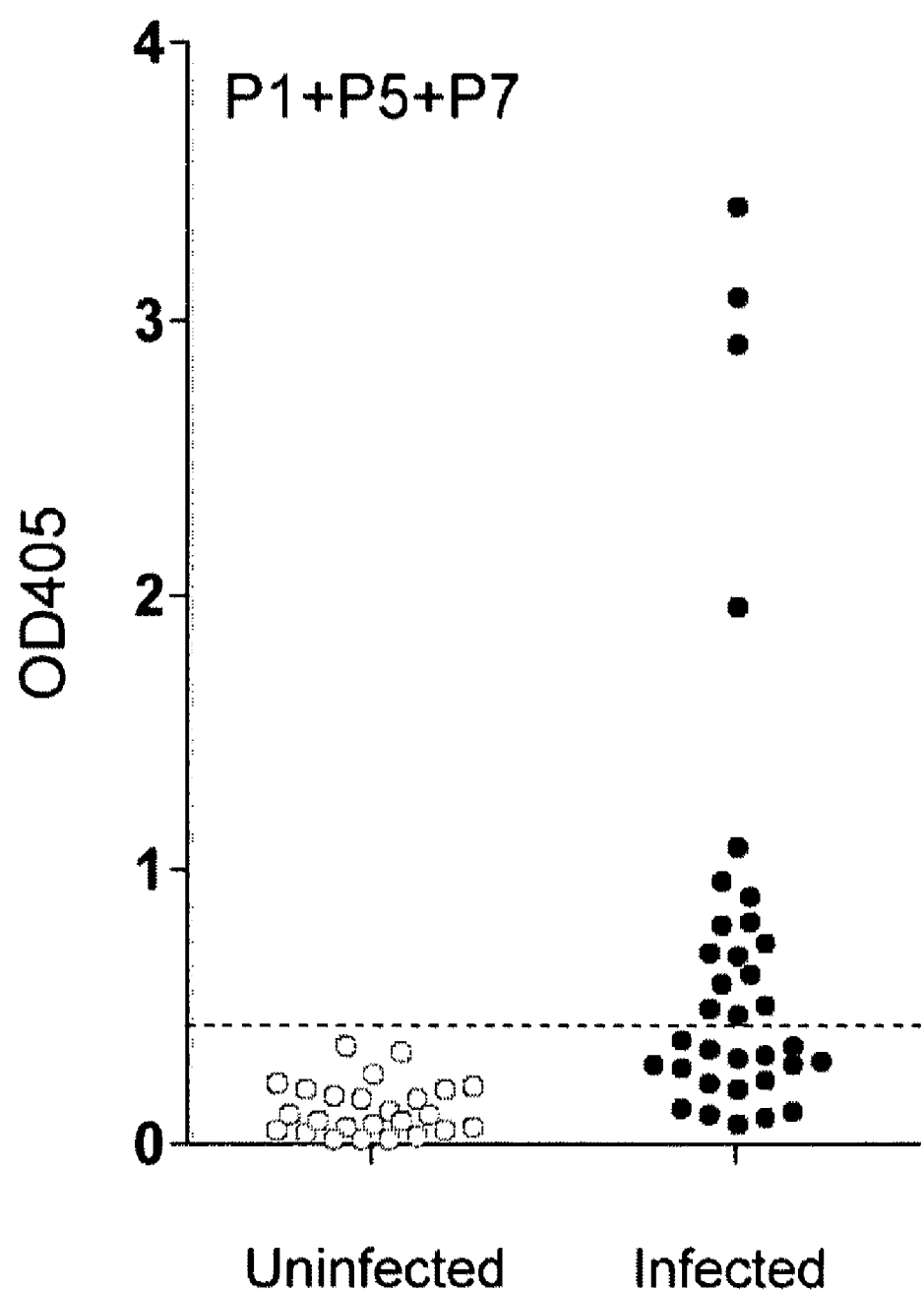

FIG. 7. Individual human serum reactivities using a combination of three immunodominant BBK07 peptides. Serum from patients diagnosed with LD (black circle) and from healthy donors (white circle) against *B. burgdorferi* lysate and a mix of peptides P1, P5, and P7 are shown from a representative experiment. Note that 17 out 34 patient sera show values above the cutoff value, indicating a greater response than amino terminal BBK07N (Coleman A. S. and Pal U., 2009, Clin. Vaccine Immunol, 16: 1569-75).

DETAILED DESCRIPTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the instant specification unless otherwise indicated. See, e.g., Sambrook et al., Molecular Cloning: A Laboratory Manual, 2d ed., Cold Spring Harbor Laboratory Press (1989) and Sambrook et al., Molecular Cloning: A Laboratory Manual, 3d ed., Cold Spring Harbor Press (2001); Ausubel et al., Current Protocols in Molecular Biology, Greene Publishing Associates (1992, and Supplements to 2000); Ausubel et al., Short Protocols in Molecular Biology: A Compendium of Methods from Current Protocols in Molecular Biology-4.sup.th Ed., Wiley & Sons (1999); Harlow and Lane, Antibodies: A Laboratory Manual, Cold Spring Harbor Laboratory Press (1990); and Harlow and Lane, Using Antibodies: A Laboratory Manual, Cold Spring Harbor Laboratory Press (1999).

A "nucleic acid molecule" of this invention refers to a polymeric form of nucleotides and includes both sense and antisense strands of RNA, cDNA, genomic DNA, and synthetic forms and mixed polymers of the above. The terms "nucleic acid," "polynucleotide," "polynucleotide sequence" and "nucleic acid sequence" refer to single-stranded or double-stranded deoxyribonucleotide or ribonucleotide polymers, or chimeras or analogues thereof. As used herein, the term optionally includes polymers or analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention encompasses complementary sequences, in addition to the sequence explicitly indicated.

The term "gene" is used broadly to refer to any nucleic acid associated with a biological function. Thus, genes include coding sequences and/or the regulatory sequences required for their expression. The term "gene" applies to a specific genomic sequence, as well as to a cDNA or an mRNA encoded by that genomic sequence.

Genes also include non-expressed nucleic acid segments that, for example, form recognition sequences for other proteins. Non-expressed regulatory sequences include "promoters" and "enhancers," to which regulatory proteins such as transcription factors bind, resulting in transcription of adjacent or nearby sequences. A "Tissue specific" promoter or enhancer is one which regulates transcription in a specific tissue type or cell type, or types.

A "gene product" is defined as a molecule expressed or encoded directly or indirectly by a gene. For example, gene products include pre-mRNA, mature mRNA, tRNA, rRNA, snRNA, u1RNA, pre-polypeptides, pro-polypeptides, mature polypeptides, post translationally modified polypeptides, processed polypeptides, functionally active polypeptides, functionally inactive polypeptides, complexed polypeptides and naturally allelic variants thereof such as single nucleotide polymorphism (SNP) variants. A single gene product may have several molecular functions and different gene products may share a single or similar molecular function. A gene product may be referred to by the accession number or common abbreviated name of the gene which expresses or encodes the gene product.

The term "level(s) of gene product" is defined as a quantifiable measurement of the gene product. The measurement may be an assay to determine the amount or mass of the product in a sample, the amount of chemically or enzymatically active product in a sample, or the amount of biologically functional product in a sample. Examples of these assays include determining relative and total RNA expression, gene copies, pre-mRNA and mature mRNA levels, knockdown levels, regulatory or surrogate marker levels, ISH, FISH, immunoassays, IHC, proteomic assays and other assays described below.

The term "vector" refers to the means by which a nucleic can be propagated and/or transferred between organisms, cells, or cellular components. Vectors include plasmids, viruses, bacteriophage, pro-viruses, phagemids, transposons, and artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that are not autonomously replicating. Most commonly, the vectors of the present invention are plasmids.

An "expression vector" is a vector, such as a plasmid, which is capable of promoting expression, as well as replication of a nucleic acid incorporated therein. Typically, the nucleic acid to be expressed is "operably linked" to a promoter and/or enhancer, and is subject to transcription regulatory control by the promoter and/or enhancer.

In the context of the invention, the term "isolated" refers to a biological material, such as a nucleic acid or a protein, which is substantially free from components that normally accompany or interact with it in its naturally occurring environment. The isolated material optionally comprises material not found with the material in its natural environment, e.g., a cell. For example, if the material is in its natural environment, such as a cell, the material has been placed at a location in the cell (e.g., genome or genetic element) not native to a material found in that environment. For example, a naturally occurring nucleic acid (e.g., a coding sequence, a promoter, an enhancer, etc.) becomes isolated if it is introduced by non-naturally occurring means to a locus of the genome (e.g., a vector, such as a plasmid or virus vector, or amplicon) not native to that nucleic acid. Such nucleic acids are also referred to as "heterologous" nucleic acids.

The term "recombinant" indicates that the material (e.g., a nucleic acid or protein) has been artificially or synthetically (non-naturally) altered by human intervention. The alteration can be performed on the material within, or removed from, its natural environment or state.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such methods as "infection," "transfection," "transformation" and "transduction." A variety of methods can be employed to introduce nucleic acids into cells, whether eukaryotic or prokaryotic, including electroporation, calcium phosphate precipitation, lipid mediated transfection (lipofection), etc.

The term "host cell" means a cell which contains a heterologous nucleic acid, such as a vector, and supports the replication and/or expression of the nucleic acid, and optionally production of one or more encoded products including a polypeptide and/or a virus. Host cells can be prokaryotic cells such as E. coli, or eukaryotic cells such as yeast, insect, amphibian, avian or mammalian cells, including human cells. Exemplary host cells in the context of the invention include Vero (African green monkey kidney) cells, human embryonic retinal cells, BHK (baby hamster kidney) cells, primary chick kidney (PCK) cells, Madin-Darby Canine Kidney (MDCK) cells, Madin-Darby Bovine Kidney (MDBK) cells, 293 cells (e.g., 293T cells), CEK cells (chicken embryo kidney) and COS cells (e.g., COS1, COS7 cells). The term host cell encompasses combinations or mixtures of cells including, e.g., mixed cultures of different cell types or cell lines (e.g., Vero, CEK, and Sf9 and High Five insect cells).

By "bind specifically" and "specific binding" as used herein it is meant the ability of the antibody to bind to a first molecular species in preference to binding to other molecular species with which the antibody and first molecular species are admixed. An antibody is said specifically to "recognize" a first molecular species when it can bind specifically to that first molecular species.

The term "epitope" includes any protein determinant capable of specific binding to an immunoglobulin or T-cell receptor. Epitopic determinants usually consist of chemically active surface groupings of molecules such as amino acids or sugar side chains and can have specific three-dimensional structural characteristics, or can be linear. An antibody is said to specifically bind an antigen when the dissociation constant is less than 1 uM, preferably less than 100 nM and most preferably less than 10 nM.

The term "subject" is used herein to refer to any subject which is susceptible to *B. burgdorferi* infection. *Borrelia burgdorferi* has been isolated or detected in 24 different species of mammals or birds. A detailed list can be found in Anderson, J. F., 1991, Scan. J. Infect. Dis. Suppl. 77, 23-34. Subjects with possible clinical complications include human and domesticated animals, such as, for example and without limitation, dogs, cats, and horses.

In one aspect of the present invention, an isolated nucleic acid encoding BBK07 is provided. The gene sequence has been deposited with GenBank at accession number accession no. AAC66153. In one embodiment, the isolated nucleic acid molecules of the present invention can be used as probes to detect and characterize gross alterations in the bbk07 gene, such as a deletion, insertion, translocation, and/or duplication of the bbk07 genomic locus, through fluorescence in situ hybridization (FISH) to chromosome spreads. See, e.g., Andreff et al. (eds.), Introduction to Fluorescence In Situ Hybridization: Principles and Clinical Applications, John Wiley & Sons (1999). The isolated nucleic acid molecules of the present invention can be used as probes to assess smaller genomic alterations using, e.g., Southern blot detection of restriction fragment length polymorphisms. The isolated nucleic acid molecules of the present invention can be used as probes to isolate genomic clones that include a nucleic acid molecule of the present invention, which thereafter can be restriction mapped and sequenced to identify deletions, insertions, translocations, and substitutions (including single nucleotide polymorphisms, SNPs) at the sequence level. Alternatively, detection techniques such as molecular beacons may be used, see Kostrikis et al., Science 279:1228-1229 (1998).

The isolated nucleic acid molecules of the present invention can also be used as probes to detect, characterize, and quantify bbk07 in, and isolate bbk07 from, transcript-derived nucleic acid samples. In one embodiment, the isolated nucleic acid molecules of the present invention can be used as hybridization probes to detect, characterize by length, and quantify mRNA by Northern blot of total or poly-A selected RNA samples. In another embodiment, the isolated nucleic acid molecules of the present invention can be used as hybridization probes to detect, characterize by location, and quantify mRNA by in situ hybridization to tissue sections. See, e.g., Schwarchzacher et al., In Situ Hybridization, Springer-Verlag N.Y. (2000). In another preferred embodiment, the isolated nucleic acid molecules of the present invention can be used as hybridization probes to measure the representation of clones in a cDNA library or to isolate hybridizing nucleic acid molecules acids from cDNA libraries, permitting sequence level characterization of mRNAs that hybridize to bbk07, including, without limitations, identification of deletions, insertions, substitutions, truncations, alternatively spliced forms and single nucleotide polymorphisms. In yet another preferred embodiment, the nucleic acid molecules of the instant invention may be used in microarrays.

All of the aforementioned probe techniques are well within the skill in the art, and are described at greater length in standard texts such as Sambrook (2001), supra; Ausubel (1999), supra; and Walker et al. (eds.), The Nucleic Acids Protocols Handbook, Humana Press (2000).

In general, a probe or primer is at least 10 nucleotides in length, more preferably at least 12, more preferably at least 14 and even more preferably at least 16 or 17 nucleotides in length. In an even more preferred embodiment, the probe or primer is at least 18 nucleotides in length, even more preferably at least 20 nucleotides and even more preferably at least 22 nucleotides in length. Primers and probes may also be longer in length. For instance, a probe or primer may be 25 nucleotides in length, or may be 30, 40 or 50 nucleotides in length. Methods of performing nucleic acid hybridization using oligonucleotide probes are well known in the art. See, e.g., Sambrook et al., 1989, supra, Chapter 11 and pp. 11.31-11.32 and 11.40-11.44, which describes radiolabeling of short probes, and pp. 11.45-11.53, which describe hybridization conditions for oligonucleotide probes, including specific conditions for probe hybridization (pp. 11.50-11.51).

Methods of performing primer-directed amplification are also well known in the art. The primers used for PCR in the examples below are bbk07 5'CCT ATT TCA AGG GCG TGA GC 3' SEQ ID NO:5, forward primer targeting a variable 3' region of the bbk07 gene, and 5' TAT GGC CAT TGC TGC ATT CT 3', SEQ ID NO:6, a reverse primer unique to the extreme 3' region of bbk07 gene. The primer pair amplifies a 139 base pair region at the 3' end of the gene. bbk07 (753 nucleotides) and bbk12 (699 nucleotides) are 90% similar with most DNA sequence conservation at the 5' end of the respective genes. Due to the nearly identical sequences of bbk07 and bbk12, the inventors tested several sets of primers and identified a primer pair that specifically detects bbk07, without cross-reactivity to bbk12. The location of primers specific for bbk07 are indicated in the complete bbk07 sequence (SEQ ID NO:7 and see Materials and Methods below). The underlined sequence in SEQ ID NO:7 indicates bbk07 sequence completely absent from bbk12. In view of the Examples and guidance provided in this application, other primer pairs which specifically amplify only bbk07 can be chosen or designed from the known bbk07 gene sequence.

Methods for performing the polymerase chain reaction (PCR) are compiled, inter alia, in McPherson, PCR Basics: From Background to Bench, Springer Verlag (2000); Innis et al. (eds.), PCR Applications: Protocols for Functional Genomics, Academic Press (1999); Gelfand et al. (eds.), PCR Strategies, Academic Press (1998); Newton et al., PCR, Springer-Verlag N.Y. (1997); Burke (ed.), PCR: Essential Techniques, John Wiley & Son Ltd (1996); White (ed.), PCR Cloning Protocols: From Molecular Cloning to Genetic Engineering, Vol. 67, Humana Press (1996); and McPherson et al. (eds.), PCR 2: A Practical Approach, Oxford University Press, Inc. (1995). Methods for performing RT-PCR are collected, e.g., in Siebert et al. (eds.), Gene Cloning and Analysis by RT-PCR, Eaton Publishing Company/Bio Techniques Books Division, 1998; and Siebert (ed.), PCR Technique: RT-PCR, Eaton Publishing Company/BioTechniques Books (1995).

PCR and hybridization methods may be used to identify and/or isolate nucleic acid molecules of the present invention including allelic variants, homologous nucleic acid molecules and fragments. PCR and hybridization methods may also be used to identify, amplify and/or isolate nucleic acid molecules of the present invention that encode homologous proteins, analogs, fusion protein or muteins of the invention. Nucleic acid primers as described herein can be used to prime amplification of nucleic acid molecules of the invention, using transcript-derived or genomic DNA as template.

Nucleic acid molecules of the present invention may be bound to a substrate either covalently or noncovalently. The substrate can be porous or solid, planar or non-planar, unitary or distributed. The bound nucleic acid molecules may be used as hybridization probes, and may be labeled or unlabeled. In a preferred embodiment, the bound nucleic acid molecules are unlabeled.

In one embodiment, the nucleic acid molecule of the present invention is bound to a porous substrate, e.g., a membrane, typically comprising nitrocellulose, nylon, or positively charged derivatized nylon. The nucleic acid molecule of the present invention can be used to detect a hybridizing nucleic acid molecule that is present within a labeled nucleic acid sample, e.g., a sample of transcript-derived nucleic acids. In another embodiment, the nucleic acid molecule is bound to a solid substrate, including, without limitation, glass, amorphous silicon, crystalline silicon or plastics. Examples of plastics include, without limitation, polymethylacrylic, polyethylene, polypropylene, polyacrylate, polymethylmethacrylate, polyvinylchloride, polytetrafluoroethylene, polystyrene, polycarbonate, polyacetal, polysulfone, celluloseacetate, cellulosenitrate, nitrocellulose, or mixtures thereof. The solid substrate may be any shape, including rectangular, disk-like and spherical. In a preferred embodiment, the solid substrate is a microscope slide or slide-shaped substrate.

The nucleic acid molecule of the present invention can be attached covalently to a surface of the support substrate or applied to a derivatized surface in a chaotropic agent that facilitates denaturation and adherence by presumed noncovalent interactions, or some combination thereof. The nucleic acid molecule of the present invention can be bound to a substrate to which a plurality of other nucleic acids are concurrently bound, hybridization to each of the plurality of bound nucleic acids being separately detectable. At low density, e.g. on a porous membrane, these substrate-bound collections are typically denominated macroarrays; at higher density, typically on a solid support, such as glass, these substrate bound collections of plural nucleic acids are colloquially termed microarrays. As used herein, the term microarray includes arrays of all densities. It is, therefore, another aspect of the invention to provide microarrays that comprise one or more of the nucleic acid molecules of the present invention. The present invention also relates to quantitative and qualitative diagnostic assays and methods for detecting, diagnosing, monitoring, staging and predicting Lyme disease by comparing the expression of bbk07 in a subject that has or may have Lyme disease, or who is at risk of developing Lyme disease, with the expression of bbk07 in a normal human control. For purposes of the present invention, "expression of a bbk07" or "bbk07 expression" means the quantity of bbk07 mRNA that can be measured by any method known in the art or the level of transcription that can be measured by any method known in the art in a bodily fluid, cell, tissue, organ or whole subject. Similarly, the term "expression of a bbk07" or "bbk07 expression" means the amount of bbk07 that can be measured by any method known in the art or the level of translation of BBK07 that can be measured by any method known in the art.

In a preferred embodiment, the expression of a bbk07 is measured by determining the amount of a mRNA that encodes an amino acid sequence corresponding to BBK07 (SEQ ID NO:1—full amino acid sequence of BBK07), a homolog, an allelic variant, or a fragment thereof. bbk07 expression may be measured by any method known in the art, such as those described supra, including measuring mRNA expression by Northern blot, quantitative or qualitative reverse transcriptase PCR (RT-PCR), microarray, dot or slot blots or in situ hybridization. See, e.g., Ausubel (1992), supra; Ausubel (1999), supra; Sambrook (1989), supra; and Sambrook (2001), supra. bbk07 transcription may be measured by any method known in the art including using a reporter gene hooked up to the promoter of a bbk07 or doing nuclear run-off assays. Alterations in mRNA structure, e.g., aberrant splicing variants, may be determined by any method known in the art, including, RT-PCR followed by sequencing or restriction analysis. As necessary, bbk07 expression may be compared to a known control, such as a normal nucleic acid, to detect a change in expression.

Expression levels of a bbk07 can be determined by any method known in the art, including PCR and other nucleic acid methods, such as ligase chain reaction (LCR) and nucleic acid sequence based amplification (NASBA). Reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction.

Hybridization to specific DNA molecules (e.g., oligonucleotides) arrayed on a solid support can be used to both detect the expression of and quantitate the level of expression of bbk07. In this approach, all or a portion of bbk07 is fixed to a substrate. A sample of interest, which may comprise RNA, e.g., total RNA or polyA-selected mRNA, or a complementary DNA (cDNA) copy of the RNA is incubated with the solid support under conditions in which hybridization will occur between the DNA on the solid support and the nucleic acid molecules in the sample of interest. Hybridization between the substrate-bound DNA and the nucleic acid molecules in the sample can be detected and quantitated by several means, including, without limitation, radioactive labeling or fluorescent labeling of the nucleic acid molecule or a secondary molecule designed to detect the hybrid.

In another aspect is an isolated peptide of the invention. An "isolated" peptide of the invention is in a form other than it occurs in nature, e.g. in a buffer, in a dry form awaiting reconstitution, as part of a kit, etc. In some embodiments, the peptide is substantially purified. The term "substantially purified", as used herein refers to a molecule, such as a peptide, that is substantially free of other proteins, lipids, carbohydrates, nucleic acids and other biological materials with which it is naturally associated. For example, a substantially pure molecule, such as a peptide, can be at least about 60%, by dry weight, preferably at least about 70%, 80%, 90%, 95%, or 99% the molecule of interest.

The identification of the peptide BBK07N spanning amino acids 18-142 of SEQ ID NO:1 was obtained from the BBK07 of the B. burgdorferi species, B. burgdorferi B31 M1, isolate A3, a clonal derivative. Active variants of this peptide include, e.g., peptides in which one or more amino acids are substituted with a conservative amino acid replacement, as are other naturally occurring variations in amino acid residues found in the bbk07 region of other *Borrelia*.

The invention includes a peptide represented by amino acids 18-142 of SEQ ID NO:1, as well as active variants of this peptide. An "active variant" of this peptide, or of other peptides described herein, refers to a peptide which retains the ability to specifically recognize (bind to) an antibody against BBK07 of Lyme disease.

An active variant peptide may contain, e.g., one or more (e.g., 1-4) amino acid additions, substitutions, deletions, insertions, inversions, fusions, and truncations or a combination of any of these. Substitutions may be of conservative or non-conservative amino acids. Conservative replacements are those that take place within a family of amino acids that are related in their side chains and chemical properties. These include, e.g., (1) acidic: aspartate, glutamate; (2) basic: lysine, arginine, histidine; (3) nonpolar: alanine, valine, leucine, isoleucine, proline, phenylalanine, methionine, tryptophan; (4) uncharged polar: glycine, asparagine, glutamine, cysteine, serine, threonine, tyrosine; (5) aliphatic: glycine, alanine, valine, leucine, isoleucine, serine, threonine, with serine and threonine optionally be grouped separately as aliphatic-hydroxyl; (6) aromatic: phenylalanine, tyrosine, tryptophan; (7) amide: asparagine, glutamine; and (9) sulfur-containing: cysteine and methionine (see, for example, Biochemistry, 2nd ed., Ed. by L. Stryer, W H Freeman and Co.: 1981). Whether a change in the amino acid sequence of a peptide results in an active variant can be readily determined by assessing the ability of the variant peptide to produce a response in e.g. an ELISA in a fashion similar to the wild-type peptide, or to competitively inhibit such a response. Peptides in which more than one replacement has been introduced can be readily tested in the same manner. Generally, between one and about four codon changes can be present in such a variant.

Another peptide of the invention is a portion of BBK07 that still binds an antibody against BBK07. In one embodiment, the peptide comprises the amino acids 18-142 of BBK07 antigen in SEQ ID NO:1, containing the amino terminal part of the protein and excluding the signal peptide. In yet another embodiment, the peptide comprises a portion of the BBK07 peptide, for example, it can consist of, e.g., 17, 18, 19, 20, 21, 22, 23 or 24 amino acids. Representative such peptides include peptides described in Table 1, for example, Peptide no. 1 (CKWHVDNPIDEATA, SEQ ID NO:2), Peptide no. 5 (ITKLTPEELENLAK, SEQ ID NO:3), and Peptide no. 7 (EKSKKEIEDQKNTK, SEQ ID NO:4). The peptide can be used alone or in combination with other BBK07 peptides for the detection of BBK07 antigen. One or more peptide can be substituted for an isolated peptide consisting of the sequence of SEQ ID NO:1 or any portion thereof, in any of the compositions of matter or methods disclosed herein. For example, the peptide can be associated with a second moiety, used as a diagnostic reagent, present in a composition comprising one or more additional polypeptides or peptides that specifically recognize antibodies to a causative agent of Lyme disease, or present in a kit for diagnosing Lyme disease.

A peptide, including a modified form thereof, which "binds specifically" to ("is specific for"; binds "preferentially" to) an antibody against a pathogenic *Borrelia* interacts with the antibody, or forms or undergoes a physical association with it, in an amount and for a sufficient time to allow detection of the antibody. By "specifically" or "preferentially" is meant that the peptide has a higher affinity, e.g. a higher degree of selectivity, for such an antibody than for other antibodies in a sample. That is, the peptide has an affinity for the antibody of at least about 2-fold higher than for other antibodies in the sample. The affinity or degree of specificity can be determined by a variety of routine procedures, including, e.g., competitive binding studies.

The peptides of the invention may be modified by a variety of techniques, such as by denaturation with heat and/or SDS. A peptide of the invention may be modified to provide an additional N- or C-terminal amino acid sequence suitable for biotinylation, e.g., cysteine or lysine; suitable for chemical lipidation, e.g., cysteine; or the like.

Peptides of the invention may be modified by any of a variety of known modifications. These include, but are not limited to, glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins such as arginylation, etc. Analogues of an amino acid (including unnatural amino acids) and peptides with substituted linkages are also included.

Such modifications are well-known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in many basic texts, such as Proteins—Structure and Molecular Properties, 2nd ed., T. E. Creighton, W.H. Freeman and Company, New York (1993). Many detailed reviews are available on this subject, such as by Wold, F., Posttranslationail Covalent Modification of Proteins, B. C. Johnson, Ed., Academic Press, New York 1-12 (1983); Seifter et al. (1990) Meth. Enzymol. 182:626-646 and Rattan et al. (1992) Ann. N.Y. Acad. Sci. 663:48-62.

Peptides of the invention that consist of any of the sequences discussed herein may be modified by any of the discussed modifications. Such peptides still "consist of" the amino acids.

Peptides of the invention may be associated with one or more further moieties. The association can be covalent or non-covalent, and can be, for example, via a terminal amino acid linker (such as Lys or Cys) or a chemical coupling agent. An additional moiety can be, e.g., a detectable label, a fusion partner (such as a chemical compound or a peptide having an epitope of another pathogenic *Borrelia*), or a substrate that immobilizes the peptide (e.g. a microwell plate, an Immobilon or nitrocellulose membrane, or latex beads).

A peptide of the invention can be fused to a fusion partner (e.g. a peptide or other moiety) that can be used to improve purification, to enhance expression of the peptide in a host cell, to aid in detection, to stabilize the peptide, etc. Examples of suitable compounds for fusion partners include polyethylene glycol, PEGylation, or other chemicals. Among the many suitable peptide or polypeptide fusion partners are, e.g., beta-galactosidase, glutathione-S-transferase, a histidine tag, etc. In some embodiments, a peptide of the invention is provided with a detectable label, such as those described below.

A peptide of the invention can be associated with a substrate that immobilizes the peptide. The substrate can be, e.g., a solid or semi-solid carrier, support or surface. The association can be covalent or non-covalent, and can be facilitated by a moiety associated with the peptide that enables covalent or non-covalent binding, such as a moiety that has a high affinity to a component attached to the carrier, support or surface. For example, the peptide can be associated with a biotin moiety, and the component associated with the surface can be avidin. The peptide can be immobilized on the solid or semi-solid surface or carrier either prior to or after the addition of the sample containing antibody.

A peptide of the present invention can be in the form of a pharmaceutically acceptable salt. Suitable acids and bases that are capable of forming salts with the peptides of the present invention are well known to those of skill in the art, and include inorganic and organic acids and bases.

A peptide of the invention can be produced using conventional chemical synthesis techniques, such as those described, e.g., in G. Barony et al., The Peptides: Analysis, Synthesis & Biology, Academic Press, pp. 3-285 (1980). Such chemically synthesized peptides can be obtained from commercial suppliers. Peptides produced by chemical synthesis can be obtained at purities exceeding about 95%. Therefore, there is typically a much reduced likelihood for undesirable cross reactivity with random antibodies than by using peptides obtained by other methods.

Alternatively, a peptide of the invention can be produced recombinantly following conventional genetic engineering techniques. To produce a recombinant peptide of the invention, a nucleic acid encoding the peptide is inserted into a suitable expression system. Generally, a recombinant molecule or vector is constructed in which the polynucleotide sequence encoding the selected peptide is operably liked to an expression control sequence permitting expression of the peptide. Numerous types of appropriate expression vectors are known in the art, including, e.g., vectors containing bacterial, viral, yeast, fungal, insect or mammalian expression systems. Methods for obtaining and using such expression vectors are well-known. For guidance in this and other molecular biology techniques used for compositions or methods of the invention, see, e.g., Sambrook et al, Molecular Cloning, A Laboratory Manual, current edition, Cold Spring Harbor Laboratory, New York; Miller et al, Genetic Engineering, 8:277-298 (Plenum Press, current edition), Wu et al, Methods in Gene Biotechnology (CRC Press, New York, N.Y., current edition), Recombinant Gene Expression Protocols, in Methods in Molecular Biology, Vol. 62, (Tuan, ed., Humana Press, Totowa, N.J., current edition), and Current Protocols in Molecular Biology, (Ausabel et al, Eds.,) John Wiley & Sons, NY (current edition), and references cited therein.

Suitable host cells or cell lines for the recombinant nucleic acids or vectors of the invention by this method include bacterial cells. For example, various strains of *E. coli* (e.g., HB101, MC1061) are well-known as host cells in the field of biotechnology. Various strains of *B. subtilis, Pseudomonas, Streptomyces*, and other bacilli and the like can also be employed in this method. Alternatively, a peptide of the invention can be expressed in yeast, insect, mammalian, or other cell types, using conventional procedures and vectors.

Thus, the present invention provides a method for producing a recombinant peptide or polypeptide, which involves transfecting or transforming, e.g., by conventional means such as electroporation, a host cell with at least one expression vector containing a polynucleotide of the invention under the control of an expression control sequence (e.g. a transcriptional regulatory sequence). The transfected or transformed host cell is then cultured under conditions that allow expression of the peptide or polypeptide. The expressed peptide or polypeptide is recovered, isolated, and optionally purified from the cell (or from the culture medium, if expressed extracellularly) by appropriate means known to one of skill in the art, including liquid chromatography such as normal or reversed phase, using HPLC, FPLC and the like; affinity chromatography (such as with inorganic ligands or monoclonal antibodies); size exclusion chromatography; immobilized metal chelate chromatography; gel electrophoresis; and the like. One of skill in the art may select the most appropriate isolation and purification techniques without departing from the scope of this invention. One skilled in the art can determine the purity of the peptide or polypeptide by using standard methods including, e.g., polyacrylamide gel electrophoresis (e.g. SDS-PAGE); column chromatography (e.g. high performance liquid chromatography (HPLC)), or amino-terminal amino acid analysis.

Included in the invention are a polynucleotide encoding and/or expressing a peptide or polypeptide of the invention, a vector comprising the polynucleotide, and a host cell comprising the polynucleotide acid or vector.

A peptide of the invention may be used in combination with one or more additional peptides or polypeptides from the same or a different protein, from the same or a different pathogenic *Borrelia* strain, wherein the additional peptide(s) or polypeptide(s) also bind specifically to an antibody against a pathogenic *Borrelia*. The combination may comprise a cocktail (a simple mixture) of individual peptides or polypeptide, or it may be in the form of a fusion peptide or polypeptide (a multimeric peptide). For example, a peptide of the invention may be fused at its N-terminus or C-terminus to another suitable peptide. Two or more copies of a peptide of the invention may be joined to one another, alone or in combination with one more additional peptides. Combinations of fused and unfused peptides or polypeptides can be used. In one embodiment, the additional peptide(s) contain B-cell and/or T-cell epitopes from a protein of a pathogenic *Borrelia*.

Suitable additional peptides or polypeptides (sometimes referred to herein as "antigenic peptides or polypeptides" or as "agents") can be derived from *Borrelia* antigens, such as OspA, OspB, DbpA, flagella-associated proteins FlaA(p37) and FlaB(p41), OspC (25 kd), BBK32, BmpA(p39), p21, p39, p66 or p83. See, e.g., Barbour et al (1984) Infect. Immun. 45, 94-100; Simpson et al. (1990) J. Clin. Microbiol. 28, 1329-1337; Hansen et al. (1988) Infect. Immun. 56, 2047-2053; Hansen et al. (1988) Infect. J. Clin. Microbiol. 26, 338-346; Wilske et al. (1986) Zentral, Bakteriol, Parsitenkd, Infektionshkr, Hyg. Abt. 1 Orig. Reihe, A. 263, 92-102; Dorward et al. (1991) J. Clin. Microbiol. 29, 1162-1170; Polypeptides or peptides derived from other microorganisms can also be used.

Another aspect of the invention is a method for diagnosing Lyme disease in a subject (e.g. for diagnosing exposure to and/or infection by a pathogenic *Borrelia*), comprising measuring a bodily fluid (which would be expected to contain antibodies) of the subject for the presence of an antibody against a causative agent of Lyme disease (e.g. an antibody capable of binding to such an agent), wherein an elevated level of antibody in the subject compared to a corresponding level of antibody in a control (such as a known unaffected subject) indicates an infection by the causative agent and/or that the subject has Lyme disease. A "causative agent for Lyme disease," as used herein, includes a pathogenic species of *B. burgdorferi*; BBK07 sequence is highly conserved in major infectious isolates of *B. burgdorferi* (Barbour, A. G. et al., 2008, Infect. Immun. 76, 3374-3389), such as, *B. burgdorferi* strain N40 and *B. burgdorferi* strain 297, which cause Lyme disease in the United States. Other species of *Borrelia* which have been implicated in Lyme disease are also included, provided they induce antibodies which can react specifically with a peptide of the invention. It is to be understood that the term "pathogenic *Borrelia*," as used herein, refers to any such pathogenic genospecies that causes Lyme disease. "Lyme disease," as used herein, refers to a disease which exhibits the characteristics as summarized in Dattwyler, R. J. and Wormser, G. "Lyme borreliosis." in Infectious Diseases Medicine and Surgery (eds.) S. Gorbach and J. Bartlett, 3rd edition, Saunders Pub. New York, N.Y., 2003 and which is caused by a pathogenic *Borrelia*.

In another aspect, BBK07 can be used to discriminate *B. burgdorferi* infection from related spirochete infection. The inventors have found that BBK07 is absent in other *Borrelia* species that cause human infection. Sequence analysis indicates that *Borrelia garinii* and *Borrelia afzelii*, the most prevalent causative agents of LD in Europe and Asia, lack an ortholog to BBK07, therefore, BBK07 reactivity could be used to discriminate human Lyme disease caused by *B. burgdorferi* from that caused by other strains.

One embodiment of this method comprises contacting (incubating, reacting) a peptide of the invention with a sample of a biological fluid (e.g serum, or cerebrospinal fluid) from a subject (e.g. human or other animal) to be diagnosed (a subject suspected of having Lyme disease). In the presence of an antibody response to infection with a pathogenic *Borrelia*, an antigen-antibody complex is formed. The antigen-antibody complex is sometimes referred to herein as an antibody-peptide complex, a peptide-antibody complex, or an antibody-epitope complex; these terms are used interchangeably. Subsequently the reaction mixture is analyzed to determine the presence or absence of this antigen-antibody complex. A variety of conventional assay formats can be employed for the detection, e.g., as ELISA or lateral flow. The presence of an elevated amount of the antibody-peptide complex indicates that the subject was exposed to and infected with a pathogenic *Borrelia* capable of causing Lyme disease. In an ELISA assay, a positive response is defined as a value 2 or 3 standard deviations greater than the mean value of a group of healthy controls. In some embodiments, a second tier assay is required to provide an unequivocal sero-diagnosis of Lyme disease.

Peptides, compositions comprising the peptides (such as diagnostic compositions), kits and methods of the invention offer a number of advantages. For example, they allow for simple, inexpensive, rapid, sensitive and accurate detection of Lyme disease, and avoid serologic cross-reactivity with other conditions with "Lyme-like" symptoms, such as myalgias, arthralgias, malaise or fever, including conditions such as syphilis, chronic arthritis, and multiple sclerosis. Furthermore, a diagnostic test of the invention (e.g. an ELISA assay) is useful in serum samples that contain antibodies produced in response to a vaccine based on the outer surface proteins of *Borrelia*; a BBK07 peptide of the invention does not cross-react with such antibodies, thereby allowing the differentiation of vaccinated individuals from individuals who were naturally infected with *B. burgdorferi*. In addition, the small size of a peptide of the invention allows it to be readily combined with other diagnostic peptides, e.g. from the same or other *Borrelia* proteins, into a multi-antigenic peptide for use in a diagnostic assay.

One aspect of the invention is an isolated peptide of the invention which binds specifically to an antibody of BBK07 induced by a causative agent of Lyme disease (a pathogenic *Borrelia*), e.g. in a sample from a subject having Lyme disease. An antibody "induced by" a pathogenic *Borrelia* is sometimes referred to herein as an antibody "against" BBK07 of the pathogenic *Borrelia*. An active variant my have one or more amino acid (e.g., conservative amino acid) replacements. Generally, a peptide of the invention is from the BBK07 protein of a pathogenic *Borrelia* species that causes Lyme disease.

Another aspect of the invention is a diagnostic reagent, comprising a peptide of the invention and, optionally, a system for detecting a complex of the peptide and a specific antibody, and/or a substrate for immobilizing the peptide.

Another aspect of the invention is a composition comprising a peptide of the invention and, optionally, one or more additional polypeptides or peptides that specifically recognize antibodies to a causative agent of Lyme disease. The additional polypeptides or peptide(s) may be used in conjunction with a peptide of the invention as part of a cocktail; or one or more of the additional polypeptides or peptides may be fused at the N-terminus and/or the C-terminus of a peptide of the invention to form a fusion peptide or polypeptide. The terms peptide and polypeptide are used interchangeably herein; for example, an amino acid consisting of three 9-15-mer peptides linked directly to one another can be referred to as either a peptide or a polypeptide.

Another aspect of the invention is a kit for diagnosing Lyme disease in a subject, which comprises a peptide of the invention and optionally comprises one or more additional peptides or polypeptides as noted above. The peptide(s) may comprise a detectable label, or the kit may include a detection system (e.g. a labeled conjugate and a reagent) for detecting a peptide which is specifically bound to an antibody in the sample. In one embodiment, the kit contains a substrate for immobilizing the peptide, such as a microwell plate, an Immobilon or nitrocellulose membrane, or latex beads.

Another aspect of the invention is a method for diagnosing Lyme disease in a subject suspected of having antibodies against BBK07 of Lyme disease (e.g. for diagnosing exposure to and/or infection by a pathogenic *Borrelia*), comprising contacting a sample from the subject a with a peptide or composition of the invention, under conditions effective for the formation of a specific peptide/antibody complex, and detecting the presence (e.g. the amount) of a peptide/antibody complex. In one embodiment, the detection method is an enzyme-linked immunosorbent assay (ELISA); and/or is carried out in vitro.

One embodiment of the invention—a composition comprising a peptide of the invention—is particularly well-suited for diagnosing *Borrelia* infections early after infection (e.g., within one week after the onset of infection). Other additional agent(s) can be added to the composition as a diagnostic agent. Among the pathogenic *Borrelia* proteins whose expression has been recognized in early human infection (e.g. to which IgM antibody appears early after infection) are OspC, BBK32, the flagella-associated protein, FlaB(p41), and, to a lesser extent, BmpA(p39), VlsE and the flagella-associated protein, FlaA(p37). Polypeptides or peptides which derive from those polypeptides are suitable for assays for early infection.

Some suitable linear epitopes which can be used for the diagnosis of early infection include peptides listed in Table 1 below, in addition to peptides identified in OspC: PVVAESP-KKP (SEQ ID NO:8), reported by Steere et al. (1987) Ann. Intern. Med. 107, 725-731; ILMTLFLFISCNNS (SEQ ID NO:9), reported by A C Steere (2001) New Engl. J. Med. 345, 115-25; and one or more epitopes contained between amino acids 161 and 210, reported by Jobe et al. (2003) Clin. Diagn. Lab. Immunol. 10, 573-8)]. The OspC peptides described in U.S. Pat. No. 6,716,574 can also be used. Other suitable regions, which have been shown to contain major cross-reactive epitopes, have been identified in FlaB(p41), e.g. residues 120 to 235. See, e.g., Crother et al., 2003, Infect. Immun. 71, 3419-3428 and Wang et al., 1999, Clin Microbial Rev 12, 633-653. Other peptides bearing either linear or conformational epitopes are known in the art.

Variants of previously identified epitopes can be readily selected by one of skill in the art, based in part on known properties of the epitopes. For example, a known epitope may be lengthened or shortened, at one or both ends, by about 1-3 amino acids; one, two or more amino acids may be substituted by conservative amino acids; etc. Furthermore, if a region of a protein has been identified as containing a suitable epitope, an investigator can "shift" the region of interest (select different sub-sequences) up to about 5 amino acids in either direction from the endpoints of the original rough region, e.g. to optimize the activity. Methods for confirming that variant peptides are suitable are conventional and routine. Methods for identifying additional epitopes are discussed in the Examples.

Polypeptides comprising linked peptides may be of any suitable length (e.g. between about 20-80 amino acids, or more), and they may contain any desirable number of linear epitopes (e.g. between about 2-5, or more). For example, between 3 to 5 peptides of about 9-15 amino acids each may be combined, optionally in the presence of suitable spacers, to generate a polypeptide of about 45-50 amino acids. A length of about 50 amino acids can be readily synthesized chemically by current technologies. Other methods may be used to generate longer peptides.

The peptides can be linked in any order. For example, a BBK07 peptide of the invention may lie at the N-terminal end of a multipeptide, at the C-terminal end of a multipeptide, or between other peptides.

In one embodiment of the invention, a composition comprising a peptide of the invention as well as one of more of the above-mentioned additional peptides (e.g. in the form of a cocktail or a fusion peptide or polypeptide) is used in a single tier assay, for detecting early/or and late stage Lyme disease. Such a peptide cocktail or fusion polypeptide can be effective in the diagnosis of Lyme disease as caused by a wide spectrum of pathogenic *Borrelia* isolates.

Fusion peptides or polypeptides (multimeric proteins) of the invention can be produced recombinantly or synthesized chemically. They may also include a peptide of the invention fused or coupled to moieties other than amino acids, including lipids and carbohydrates.

One aspect of the invention is a method for detecting Lyme disease in a subject suspected of having antibody against a causative agent of Lyme disease. The diagnostic method is useful for diagnosing subjects exhibiting the clinical symptoms of, or suspected of having, Lyme disease.

The subject can be any subject (patient) in which antibodies can be made against BBK07 of the causative agent and detected. Typical subjects include vertebrates, such as mammals, including wildlife (e.g. mice and chipmunks), dogs, cats, non-human primates and humans.

In one embodiment, the diagnostic method involves detecting the presence of naturally occurring antibodies against BBK07 of pathogenic *Borrelia* (e.g. *B. burgdorferi*) which are produced by the infected subject's immune system in its biological fluids or tissues, and which are capable of binding specifically to a peptide of the invention or combinations of a peptide of the invention and, optionally, one or more suitable additional antigenic polypeptides or peptides.

One embodiment of the invention is a diagnostic immunoassay method, which includes (1) taking a sample of body fluid or tissue likely to contain antibodies; (2) contacting the sample with a peptide of the invention, under conditions effective for the formation of a specific peptide-antibody complex (for specific binding of the peptide to the antibody), e.g., reacting or incubating the sample and a peptide; and (3) assaying the contacted (reacted) sample for the presence of an antibody-peptide reaction (e.g., determining the amount of an antibody-peptide complex).

Phrases such as "sample containing an antibody" or "detecting an antibody in a sample" are not meant to exclude samples or determinations (detection attempts) where no antibody is contained or detected. In a general sense, this invention involves assays to determine whether an antibody produced in response to infection with a pathogenic *Borrelia* is present in a sample, irrespective of whether or not it is detected.

Conditions for reacting peptides and antibodies so that they react specifically are well-known to those of skill in the art. See, e.g., Current Protocols in Immunology (Coligan et al., editors, John Wiley & Sons, Inc) or the Examples herein.

The diagnostic method comprises taking a sample of body fluid or tissue likely to contain antibodies. The antibodies can be, e.g., of IgG, IgE, IgD, IgM, or IgA type. Generally, IgM and/or IgA antibodies are detected, e.g. for the detection of early infection. The sample is preferably easy to obtain and may be serum or plasma derived from a venous blood sample or even from a finger prick. Tissue from other body parts or other bodily fluids, such as cerebrospinal fluid (CSF), saliva, gastric secretions, mucus, etc. are known to contain antibodies and may be used as a source of the sample.

Once the peptide antigen and sample antibody are permitted to react in a suitable medium, an assay is performed to determine the presence or absence of an antibody-peptide reaction. Among the many types of suitable assays, which will be evident to a skilled worker, are immunoprecipitation and agglutination assays.

In embodiments of the invention, the assay may comprise (1) immobilizing the antibody(s) in the sample, adding a peptide of the invention, and then detecting the degree of antibody bound to the peptide, e.g. by the peptide being labeled or by adding a labeled substance (conjugate, binding partner), such as a labeled antibody, which specifically recognizes the peptide; (2) immobilizing a peptide of the invention, adding the sample containing an antibody(s), and then detecting the amount of antibody bound to the peptide, e.g. by adding a labeled substance (conjugate, binding partner), such as a labeled antibody, which specifically recognizes the antibody; or (3) reacting the peptide and the sample containing antibody(s) without any of the reactants being immobilized, and then detecting the amount of complexes of antibody and peptide, e.g. by the peptide being labeled or by adding a labeled substance (conjugate, binding partner), such as a labeled antibody, which specifically recognizes the peptide.

Immobilization of a peptide of the invention can be either covalent or non-covalent, and the non-covalent immobilization can be non-specific (e.g. non-specific binding to a polystyrene surface in e.g. a microtiter well). Specific or semi-specific binding to a solid or semi-solid carrier, support or surface, can be achieved by the peptide having, associated with it, a moiety which enables its covalent or non-covalent binding to the solid or semi-solid carrier, support or surface. For example, the moiety can have affinity to a component attached to the carrier, support or surface. In this case, the moiety may be, e.g., a biotin or biotinyl group or an analogue thereof bound to an amino acid group of the peptide, such as 6-aminohexanoic acid, and the component is then avidin, streptavidin or an analogue thereof. An alternative is a situation in which the moiety has the amino acid sequence of 6-Histidines and the carrier comprises a Nitrilotriacetic Acid derivative (NTA) charged with Ni++ ions. Among suitable carriers, supports or surface are, e.g., magnetic beads or latex of co-polymers such as styrene-divinyl benzene, hydroxylated styrene-divinyl benzene, polystyrene, carboxylated polystyrene, beads of carbon black, non-activated or polystyrene or polyvinyl chloride activated glass, epoxy-activated porous magnetic glass, gelatin or polysaccharide particles or other protein particles, red blood cells, mono- or polyclonal antibodies or Fab fragments of such antibodies.

The protocols for immunoassays using antigens for detection of specific antibodies are well known in art. For example, a conventional sandwich assay can be used, or a conventional competitive assay format can be used. For a discussion of some suitable types of assays, see Current Protocols in Immunology (supra). In a preferred assay, a peptide of the invention is immobilized to the solid or semi-solid surface or carrier by means of covalent or non-covalent binding, either prior to or after the addition of the sample containing antibody.

Devices for performing specific binding assays, especially immunoassays, are known and can be readily adapted for use in the present methods. Solid phase assays, in general, are easier to perform than heterogeneous assay methods which require a separation step, such as precipitation, centrifugation, filtration, chromatography, or magnetism, because separation of reagents is faster and simpler. Solid-phase assay devices include microtiter plates, flow-through assay devices, dipsticks and immunocapillary or immunochromatographic immunoassay devices.

In embodiments of the invention, the solid or semi-solid surface or carrier is the floor or wall in a microtiter well; a filter surface or membrane (e.g. a nitrocellulose membrane or a PVDF (polyvinylidene fluoride) membrane, such as an Immobilon membrane); a hollow fiber; a beaded chromatographic medium (e.g. an agarose or polyacrylamide gel); a magnetic bead; a fibrous cellulose matrix; an HPLC matrix; an FPLC matrix; a substance having molecules of such a size that the molecules with the peptide bound thereto, when dissolved or dispersed in a liquid phase, can be retained by means of a filter; a substance capable of forming micelles or participating in the formation of micelles allowing a liquid phase to be changed or exchanged without entraining the micelles; a water-soluble polymer; or any other suitable carrier, support or surface.

In some embodiments of the invention, the peptide is provided with a suitable label which enables detection. Conventional labels may be used which are capable, alone or in concert with other compositions or compounds, of providing a detectable signal. Suitable detection methods include, e.g., detection of an agent which is tagged, directly or indirectly, with a fluorescent label by immunofluorescence microscopy, including confocal microscopy, or by flow cytometry (FACscan); detection of a radioactively labeled agent by autoradiography; electron microscopy; immunostaining; subcellular fractionation, or the like. In one embodiment, a radioactive element (e.g. a radioactive amino acid) is incorporated directly into a peptide chain; in another embodiment, a fluorescent label is associated with a peptide via biotin/avidin interaction, association with a fluorescein conjugated antibody, or the like. In one embodiment, a detectable specific binding partner for the antibody is added to the mixture. For example, the binding partner can be a detectable secondary antibody that binds to the first antibody. This secondary antibody can be labeled, e.g., with a radioactive, enzymatic, fluorescent, luminescent, or other detectable label, such as an avidin/biotin system.

A "detection system" for detecting bound peptide, as used herein, may comprise a detectable binding partner, such as an antibody specific for the peptide. In one embodiment, the binding partner is labeled directly. In another embodiment, the binding partner is attached to a signal generating reagent, such as an enzyme that, in the presence of a suitable substrate, can produce a detectable signal. A surface for immobilizing the peptide may optionally accompany the detection system.

In embodiments of the invention, the detection procedure comprises visibly inspecting the antibody-peptide complex for a color change, or inspecting the antibody-peptide complex for a physical-chemical change. Physical-chemical changes may occur with oxidation reactions or other chemical reactions. They may be detected by eye, using a spectrophotometer, or the like.

In one embodiment of the method, the peptide, or a mixture of peptides, is electro- or dot-blotted onto nitrocellulose paper. Subsequently, the biological fluid (e.g. serum or plasma) is incubated with the blotted antigen, and antibody in the biological fluid is allowed to bind to the antigen(s). The bound antibody can then be detected, e.g. by standard immunoenzymatic methods.

In another embodiment of the method, latex beads are conjugated to the antigen(s) of the invention. Subsequently, the biological fluid is incubated with the bead/peptide conjugate, thereby forming a reaction mixture. The reaction mixture is then analyzed to determine the presence of the antibodies.

One preferred assay for the screening of blood products or other physiological or biological fluids is an enzyme linked immunosorbant assay, i.e., an ELISA. Typically in an ELISA, the isolated antigen(s) of the invention is adsorbed to the surface of a microtiter well directly or through a capture matrix (i.e., antibody). Residual, non-specific protein-binding sites on the surface are then blocked with an appropriate agent, such as bovine serum albumin (BSA), heat-inactivated normal goat serum (NGS), or BLOTTO (a buffered solution of nonfat dry milk which also contains a preservative, salts, and an antifoaming agent). The well is then incubated with a biological sample suspected of containing specific anti-pathogenic *Borrelia* (e.g. *B. burgdoferi*) antibody. The sample can be applied neat, or more often it can be diluted, usually in a buffered solution which contains a small amount (0.1-5.0% by weight) of protein, such as BSA, NGS, or BLOTTO. After incubating for a sufficient length of time to allow specific binding to occur, the well is washed to remove unbound protein and then incubated with an optimal concentration of an appropriate anti-immunoglobulin antibody (e.g., for human subjects, an anti-human immunoglobulin from another animal, such as dog, mouse, cow, etc.) that is conjugated to an enzyme or other label by standard procedures and is dissolved in blocking buffer. The label can be chosen from a variety of enzymes, including horseradish peroxidase (HRP), β-galactosidase, alkaline phosphatase, glucose oxidase, etc. Sufficient time is allowed for specific binding to occur again, then the well is washed again to remove unbound conjugate, and a suitable substrate for the enzyme is added. Color is allowed to develop and the optical density of the contents of the well is determined visually or instrumentally (measured at an appropriate wave length). The cutoff OD value may be defined as the mean OD±3 standard deviations (SDs) of at least 50 serum samples collected from individuals from an area where Lyme disease is not endemic, or by other such conventional definitions. In the case of a very specific assay, OD±2 SD can be used as a cutoff value.

In one embodiment of an ELISA, a peptide of the invention is immobilized on a surface, such as a ninety-six-well ELISA plate or equivalent solid phase that is coated with streptavidin or an equivalent biotin-binding compound at an optimal concentration in an alkaline coating buffer and incubated at 4° C. overnight. After a suitable number of washes with standard washing buffers, an optimal concentration of a biotinylated form of a composition/antigen of this invention dissolved in a conventional blocking buffer is applied to each well; a sample is added; and the assay proceeds as above.

See the Examples for typical conditions for performing ELISA assays.

Another useful assay format is a lateral flow format. Antibody to human or animal antibody or staph A or G protein antibodies is labeled with a signal generator or reporter (i.e. colloidal gold) that is dried and placed on a glass fiber pad (sample application pad). The diagnostic peptide is immobilized on membrane, such as a PVDF (polyvinylidene fluoride) membrane (e.g an Immobilon membrane (Millipore)) or a nitrocellulose membrane. When a solution of sample (blood, serum, etc) is applied to the sample application pad, it dissolves the colloidal gold labeled reporter and this binds to all antibodies in the sample. This mixture is transported into the next membrane (PVDF or nitrocellulose containing the diagnostic peptide) by capillary action. If antibodies against the diagnostic peptide are present, they bind to the diagnostic peptide striped on the membrane generating a signal. An additional antibody specific to the colloidal gold labeled antibody (such as goat anti-mouse IgG) is used to produce a control signal.

It should be understood by one of skill in the art that any number of conventional protein assay formats, particularly immunoassay formats, may be designed to utilize the isolated peptides of this invention for the detection of pathogenic Borrelia (e.g. B. burgdorferi) infection a subject. This invention is thus not limited by the selection of the particular assay format, and is believed to encompass assay formats that are known to those of skill in the art.

Reagents for ELISA or other assays according to this invention can be provided in the form of kits. Such kits are useful for diagnosing infection with a pathogenic Borrelia (e.g. a B. burgdorferi), using a sample from a subject (e.g. a human or other animal). Such a diagnostic kit can contain an peptide of the invention (and, if desired, additional peptides as discussed above) and, optionally, a system for (means enabling) detection of a peptide of the invention bound to an antibody against a protein from a pathogenic Borrelia, and/or a surface to which the peptide can be bound. In one embodiment, a kit contains a mixture of suitable peptides or means for preparing such mixtures, and/or reagents for detecting peptide-antibody complexes.

The kit can include microtiter plates to which the peptide(s) of the invention have been pre-adsorbed, another appropriate assay device, various diluents and buffers, labeled conjugates or other agents for the detection of specifically bound antigens or antibodies, and other signal-generating reagents, such as enzyme substrates, cofactors and chromogens. Other components of a kit can easily be determined by one of skill in the art. Such components may include coating reagents, polyclonal or monoclonal capture antibodies specific for a peptide of the invention, or a cocktail of two or more of the antibodies, purified or semi-purified extracts of these antigens as standards, MAb detector antibodies, an anti-mouse or anti-human antibody with indicator molecule conjugated thereto, an ELISA plate prepared for absorption, indicator charts for colorimetric comparisons, disposable gloves, decontamination instructions, applicator sticks or containers, a sample preparatory cup, etc. In one embodiment, a kit comprises buffers or other reagents appropriate for constituting a reaction medium allowing the formation of a peptide-antibody complex. Such kits provide a convenient, efficient way for a clinical laboratory to diagnose infection by a pathogenic Borrelia, such as a B. burgdorferi.

Another aspect of the invention is an isolated antibody, antigen-specific antibody fragment, or other specific binding partner, which is specific for a peptide of the invention, e.g., wherein said antibody, antigen-specific antibody fragment, or specific binding partner is specific for BBK07 or one of the other BBK07 peptides of the invention. Antibodies, e.g. polyclonal, monoclonal, recombinant, chimeric, humanized, single-chain, Fab, and fragments thereof, can be prepared according to any desired method. See also screening recombinant immunoglobulin libraries (e.g., Orlandi et al. (1989) Proc. Natl. Acad. Sci. USA 86, 3833-3837; Huse et al. (1989) Science 256, 1275-1281); and in vitro stimulation of lymphocyte populations (Winter et al. (1991) Nature 349, 293-299). The antibodies can be IgM, IgG, subtypes, IgG2a, IgG1, etc. Antibodies can be used from any source, including, goat, rabbit, mouse, chicken, etc. An antibody specific for a peptide means that the antibody recognizes a defined sequence of amino acids within or including the peptide. Other specific binding partners include, e.g., aptamers and PNA. The preparation of polyclonal antibodies is well-known to those skilled in the art. See, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992). The preparation of monoclonal antibodies likewise is conventional. See, for example, Kohler & Milstein (1975) Nature 256, 495; Coligan et al., sections 2.5.1-2.6.7; and Harlow et al., Antibodies: A Laboratory Manual, page 726 (Cold Spring Harbor Pub. 1988).

An isolated antibody, antigen-specific antibody fragment, or other specific binding partner of the invention can be used for a variety of applications, including therapeutic and diagnostic applications. By an "isolated" antibody is meant herein an antibody molecule that is removed from its original environment (e.g., the natural environment if it is naturally occurring), and is isolated or separated from at least one other component with which it is naturally associated. For example, a naturally-occurring antibody present in its natural living host is not isolated, but the same antibody, separated from some or all of the coexisting materials in the natural system, is isolated. Such antibodies could be part of a composition, and still be isolated in that such composition is not part of its natural environment One aspect of the invention is a method for detecting in a subject the presence of a naturally occurring BBK07 antigen, itself, in its association with a pathogenic Borrelia, using an isolated antibody of the invention. The method can be used to determine that a subject has been exposed to, or infected by, a pathogenic Borrelia. In one embodiment, the method comprises contacting a sample (e.g. a bodily fluid or tissue suspected of containing a pathogenic Borrelia) from a subject with an antibody of the invention, under conditions effective for the formation of a specific antigen-antibody reaction. Preferably, the antibody is conventionally labeled, either directly or indirectly, for detection, e.g., with an enzyme such as HRP, avidin or biotin, chemiluminescent reagents, etc. Following the binding of the antibody to the antigen, excess labeled antibody is optionally removed, and the reaction mixture is analyzed to determine the presence or absence of the antigen-antibody complex and the amount of label associated therewith.

In one embodiment, a monoclonal or polyclonal antibody of the invention (which is capable of binding to the antigen) is bound to an ELISA plate. A sample, such as a biological fluid, is incubated on the antibody-bound plate and washed. Detection of an antigen-antibody complex and qualitative measurement of the labeled antibody are performed conventionally.

Other useful assay formats include the filter cup and dipstick. In the former assay, an antibody of the invention is fixed to a sintered glass filter to the opening of a small cap. The biological fluid or sample (e.g., about 5 mL) is worked through the filter. If the antigen is present (e.g. following infection with a pathogenic *Borrelia*), it will bind to the filter which can then be visualized through a second antibody/detector. The dipstick assay involves fixing an antigen or antibody to a filter, which is then dipped in the biological fluid, dried and screened with a detector molecule.

Kits for conducting this or other assay methods, using an antibody, antigen-specific antibody fragment, or other specific binding partner of the invention, are also included in the invention.

Much of the preceding discussion is directed to the detection of antibodies against pathogenic *Borrelia*. However, it is to be understood that the discussion also applies to the detection of primed T-cells, either in vitro or in vivo.

It is expected that a cell-mediated immune response (e.g. a T-helper response) is generated, since IgG is produced. It is therefore expected that it will be possible to determine the immunological reactivity between primed T-cells and a peptide of the invention. In vitro this can be done by incubating T-cells isolated from the subject with a peptide of the invention and measuring the immunoreactivity, e.g. by measuring subsequent T-cell proliferation or by measuring release of cytokines from the T-cells, such as IFN-gamma; these methods are well-known in the art.

When a method of the invention is carried out in vivo, any of a variety of conventional assays can be used. For example, one can perform an assay in the form of a skin test, i.e. by intradermally injecting, in the subject, a peptide of the invention A positive skin reaction at the location of injection indicates that the subject has been exposed to and infected with a pathogenic *Borrelia* capable of causing Lyme disease, and a negative skin response at the location of injection indicates that the subject has not been so exposed/infected. This or other in vivo tests rely on the detection of a T-cell response in the subject.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Bacteria, ticks and mice. Isolate A3, a clonal derivative of *Borrelia burgdorferi* B31 M1 and a generous gift from Dr. Patricia Rosa was used throughout the study. Bacteria were grown in BSK-II media at 34° C. The Ixodes scapularis ticks used in this study were maintained in the laboratory as described (Pal, U. et al., Cell 119, 457-468). C3H/HeN mice were purchased from the National Cancer Institute. All animal procedures were performed in compliance with the guidelines and with the approval of the Institutional Animal Care and Use Committee. Unless otherwise stated, single intradermal needle-inoculation of $10^5$ *B. burgdorferi* cells was used to infect each mouse. For generation of immunized seaim. each mouse was injected with 100 ug of *B. burgdorferi* sonicate (5 mice/group) intradermally. As injections with lysed spirochetes were performed without an adjuvant, all booster injections were performed at weekly intervals for 9 weeks. Polyclonal antibodies against truncated BBK07 protein representing amino terminal region of the mature protein (BBK07N) were obtained by injecting mice intradermally with recombinant protein (10 pg/animal) emulsified in complete Freund's adjuvant once, and twice in incomplete Freund's adjuvant (Sigma, St. Louis, Mo.) at 10 day intervals. Serum was collected and pooled 10 days after final injection (Coleman, A. S, et al., 2008, PLoS ONE 3, 3010e).

Purification of recombinant proteins. The recombinant protein fragment BBK07N, containing amino terminal part of the protein and excluding the signal peptide, amino acids 18-142 of SEQ ID NO:1, was fused to an N-terminal 6-histidine tag for purification on the pET302/NT-His Champion vector (Invitrogen, Carlsbad, Calif.). The following oligonucleotide primers were used to construct the expression vector: forward primer (5' AAT CTA GAA TGT GGC ATG TAG ACA ATC CCA TTG 3', Xbal site italicized, SEQ ID NO:10), reverse primer (5'CCG GGA TCC ATT ACA TCT TTA GTC CAT TCT T 3'. BamHI site italicized, SEQ ID NO:11). Purification was performed using commercial cell lysis buffer (FastBreak, Promega, Madison, Wis.) and MagneHis nickel particles (Promega) according to the manufacturer's instructions. Recombinant VlsE was a generous gift from Fang Ting Liang from Louisiana State University. Recombinant BmpA (Pal, U. et al., 2008, J. Exp. Med. 205, 133-141), Lp6.6 (Lahdenne, P. et al., 1997, Infect. Immun. 65, 412-421), OspC (Pal, U. et al., 2004, J. Clin. Invest. 113, 220-230) and BbCRASP-2 (Coleman, A. S. et al., 2008, supra) were purified as detailed.

Gene expression analysis. Infected ticks (3 ticks per time point), as well as infected mouse skin, hearts, and tibiotarsal joints (3 mice per time point) were homogenized using mortar and pestle under liquid nitrogen, and total RNA extracted using TRIzol reagent (Invitrogen, Carlsbad, Calif.). RNA from log-phase in vitro-grown *B. burgdorferi* ($10^7$ spirochetes/ml) was also isolated using TRIzol reagent (Invitrogen). The purified RNA was treated with DNase I (NEB) to reduce DNA contamination. One microgram of total RNA from each sample was used to synthesize cDNA using AffinityScript first-strand cDNA synthesis (Stratagene, LaJolla, Calif.). Quantitative RT-PCR (qRT-PCR) analysis was performed on 50 pg of each cDNA using iQ SybrGreen Supermix (BioRad, Hercules, Calif.). To help protect against DNA contamination, cDNA was compared to an equal concentration of template RNA to measure the contribution of DNA to the final results. Standard curves for flaB and bbkOl were generated using *B. burgdorferi* genomic DNA purified by DNeasy Blood and Tissue Kit (Qiagen, Valencia, Calif.). The following primers were used for qPCR: flaB (5' TTC AAT CAG GTA ACG GCA CA, (SEQ ID NO:12) GAC GCT TGA GAC CCT GAA AG 3')(SEQ ID NO:13), bbk07 (5' CCT ATT TCA AGG GCG TGA GC (SEQ ID NO:5), TAT GGC CAT TGC TGC ATT CT 3', SEQ ID NO:6), bbk12 (5' GCT GAA AAT TCG GTA AGC GTT T (SEQ ID NO:14), TAA GTT CGC TGC ATA CAC CTT CA 3', SEQ ID NO:15).

SEQ ID NO:7 below is the bbk07 nucleotide sequence with primer location in bold. Underlined nucleotides indicates bbk07 sequence completely absent from bbk12.

ATGAGTAAACTAATATTGGCAATATCTATACTGCTAATAATTTCATGTAA

ATGGCATGTAGACAATCCCATTGATGAAGCAACTGCAGAAAGTAAATCAG

CACTAACATCTGTTGATCAAGTATTAGATGAGATAAGTGAAGCTACAGGT

```
                                            -continued
CTAAGTTCGGAAAAAATCACAAAATTAACTCCGGAAGAGCTAGAAAATTT

AGCAAAGGAAGCTCAAGATGATTCTGAAAAATCCAAAAAAGAAATTGAAG

ATCAAAAAAATACCAAGGAAAGTAAAAACATAGAAGTAAAGGATACTCCT

CGCTTAATCAAATTGATTAAGAATTCATCAGAAAAAATTGATTCGGTTTT

TCAAACACTAATTAATATAGGTTATAATGCTACCTATGCAGCCAAAAGTA

ATTTGAAGAATGGACTAAAGATGGTGAAATTACTGGATGAGTTGCTAAAA

ATATCGGTAAGTAGCAATGGTGATAAAAGTACCCAAAAATACAATGAACT

TAAAACCGTTGTAAATAGGTTTAATGCTGAAAATTCAGCGATAAAGGTAC

CATTAGAAAATGGTAGTAAAATTGAAGCCAAAAAGTGCATAAAAACTCTT

ATGACCAATGTGGAAACCTATTTCAAGGGCGTGAGCACCGAACTCAAAGA

TAAAAAAGACGACAAATATACTAAAATATTGGCAGCTTTGAGTGAGGCAG

CCAATAAAATAGAGAATGCAGCAATGGCCATACATTTGTGCTTTAATAAT

TAA
```

Proteinase K accessibility assay. Proteinase K accessibility assays were performed as described (BROOKS, C. S., ET AL., 2006, INFECT. IMMUN. 74, 296-304), with the following modifications. *B. burgdorferi* ($1 \times 10^9$) were gently washed three times in 1 ml of PBS (pH 7.4) and collected by centrifugation at 4,000×g for 5 min. Washed spirochetes were then gently resuspended in 100 ul of PBS and split into two equal 50 ul 5 volumes. One aliquot received 10 ug of proteinase K (PK) (Sigma) in PBS while the other aliquot received an equal volume of PBS without PK. Both aliquots were incubated for 20 minutes at room temperature, and then washed 3 times with 1 ml PBS with 1 mM phenylmethylsulfonylfluoride (Sigma, St. Louis, Mo.) to stop PK activity. After washing, the spirochetes were resuspended in PBS and used for immunoblot analysis.

Serum, Immunoblots and ELISA. Polyclonal BBK07N antisera was used for immunoblot at 1:2000 dilution in 5% skim milk. FlaB and OspA antisera was used as described (Yang, X. et al., 2009, PLoS Pathog 5, e1000326). For ELISA, antigens (100-200 ng/well) were coated on PolySorp immunoplates (Nunc, Rochester, N.Y.) in 50 mM carbonate-bicarbonate buffer, pH 9.6 (Sigma). All other murine sera were diluted to 1:5000 in 1% bovine serum albumin (BSA) in TBS-T (50 mM Tris, 150 mM NaCl, 0.05% Tween-20, pH 7.5). Thirty-five serum samples from humans with a clinical history of LD, collected from the CDC Lyme patient serum panel, were used in the ELISA. The infected sera were collected from patients with clinical symptoms associated either with early or disseminated phases of LD. The intervals of serum collection from patients ranged from 2 weeks to 13 years following onset of disease. Five serum samples from normal individuals residing in non-endemic areas for LD were collected from CDC, while additional serum samples from twenty individuals that tested negative for *B. burgdorferi* infection were provided by Marylou Breitentein at Yale University. The 25 control sera were used to define the cut-off value for each antigen (mean plus 2 SD) (Panelius, J. et al., 2003, J. Neurol. 250, 1318-1327).

Human sera were diluted to 1:1000 in 1% BSA in TBS-T. Secondary antibodies against IgG, conjugated to horseradish peroxidase, were used with the following dilutions: goat anti-mouse 1:10000, goat anti-human 1:5000 (KPL). All steps were carried out either for one hour at 25° C., or overnight at 4° C. Immunoblots were developed on HyBlot CL film (Denville, Metuchen, N.J.) using ECL Detection Reagent (GE Healthcare, Piscataway, N.J.). ELISA results were quantified using SureBlue TMB 6 microwell peroxidase Substrate and TMB Stop Solution (KPL, Gaithersburg, Md.).

Statistics. Results are expressed as the mean±standard error of the mean (SEM). The significance of the difference between the mean values of the groups was evaluated by two-tailed Student/-test.

BBK07 peptide library. A library of 23 overlapping peptides (P1-P23) covering full-length BBK07 was synthesized commercially using the PEPscreen system (Sigma, St. Louis, Mo.) as indicated in Table 1. The peptides were labeled with N-terminal biotin, and dissolved in dimethyl sulfoxide.

Human serum and ELISA for synthetic peptides. Thirty-four serum samples from human patients with a clinical history of LD, as well as five samples from normal individuals residing in non-endemic LD areas were collected from the CDC Lyme patient serum panel. Additional serum samples from twenty individuals that tested negative for *B. burgdorferi* infection were provided by Marylou Breitentein at Yale University. The twenty-five total control sera were used to define the cutoff value in each assay (mean plus 3 SD). For ELISA, antigens were diluted in 50 mM carbonate-bicarbonate buffer, pH 9.6, and coated on MaxiSorp plates. Recombinant BBK07N and *B. burgdorferi* lysate were coated using 100 ng per well, and synthetic peptides using 5 ug per well. The plates were blocked using 1% bovine serum albumin in PBS-T (phosphate buffered saline with 0.05% Tween-20), and plates were washed extensively between all steps with PBS-T. Human sera were diluted 1:200 in 1% BSA in PBS-T. Secondary antibodies antibodies against human IgG raised in goat, conjugated to horseradish peroxidase (KPL, Gaithersburg, Md.) were used with a dilution of 1:5000. All steps were carried out either for one hour at 25° C. or overnight at 4° C. ELISA results were quantified using SureBlue TMB Substrate and TMB Stop Solution (KPL).

Example 1

Indentification of *B. burgdorferi* genes that are induced in infected murine hosts. To identify *B. burgdorferi* genes that are highly expressed in murine joints, we employed quantitative RT-PCR (qRT-PCR) approach to assess the spirochete transcriptome in mice, during the development of inflammation in joints. A total of 100 spirochete genes were selected for expression analysis, based on their putative association with the spirochete membrane, as determined by their database annotation and in silico analyses for extracellular exposure. Groups of mice (5 animals/group) were infected with *B. burgdorferi* ($10^5$ spirochetes/mouse) and samples of skin, bladder and tibiotarsal joints were collected and frozen in liquid nitrogen at one-week intervals between 1 and 4 weeks of infection. Total RNA was extracted from tissue samples and used for qRT-PCR analysis of *B. burgdorferi* gene-specific mRNA. The expression of each gene in different murine tissues was tabulated, as gene expression levels relative to the flab expression in corresponding tissues derived from two independent mouse experiments. The data revealed that selected *B. burgdorferi* genes displayed reproducible expression in mice, and that many of the in vivo-expressed genes displayed high expression levels in mice (data not shown), compared to in vitro expression (data not shown). We chose bbk07 as the focus of our study through a consideration of the detailed expression patterns of the gene during the genesis of murine disease, immunogenicity, surface exposure, sequence conservation and published information. No published information on the expression or function of BBK07 is available.

We detected expression of bbk07 in mice throughout spirochete infection with high expression preceding the development of disease, between day 5 and 10 of infection. bbk07 is variably expressed in different murine tissues with higher levels in skin and joints. Western blot analysis was performed, which indicated that BBK07 antibody is generated during *B. burgdorferi* infection of the murine host, which is consistent with the detection of BBK07 antibody in human patients with Lyme borreliosis. Although bbk07 is conserved amongst *B. burgdorferi*, like many plasmid-borne *B. burgdorferi* genes, BBK07 has no orthologs in related sensu lato spirochetes *B. afzellii* and *B. garinii*, indicating the unique function of this antigen in the *B. burgdorferi* life cycle, which is the most arthritogenic of the sensu lato spirochetes.

Example 2

Figure 1:
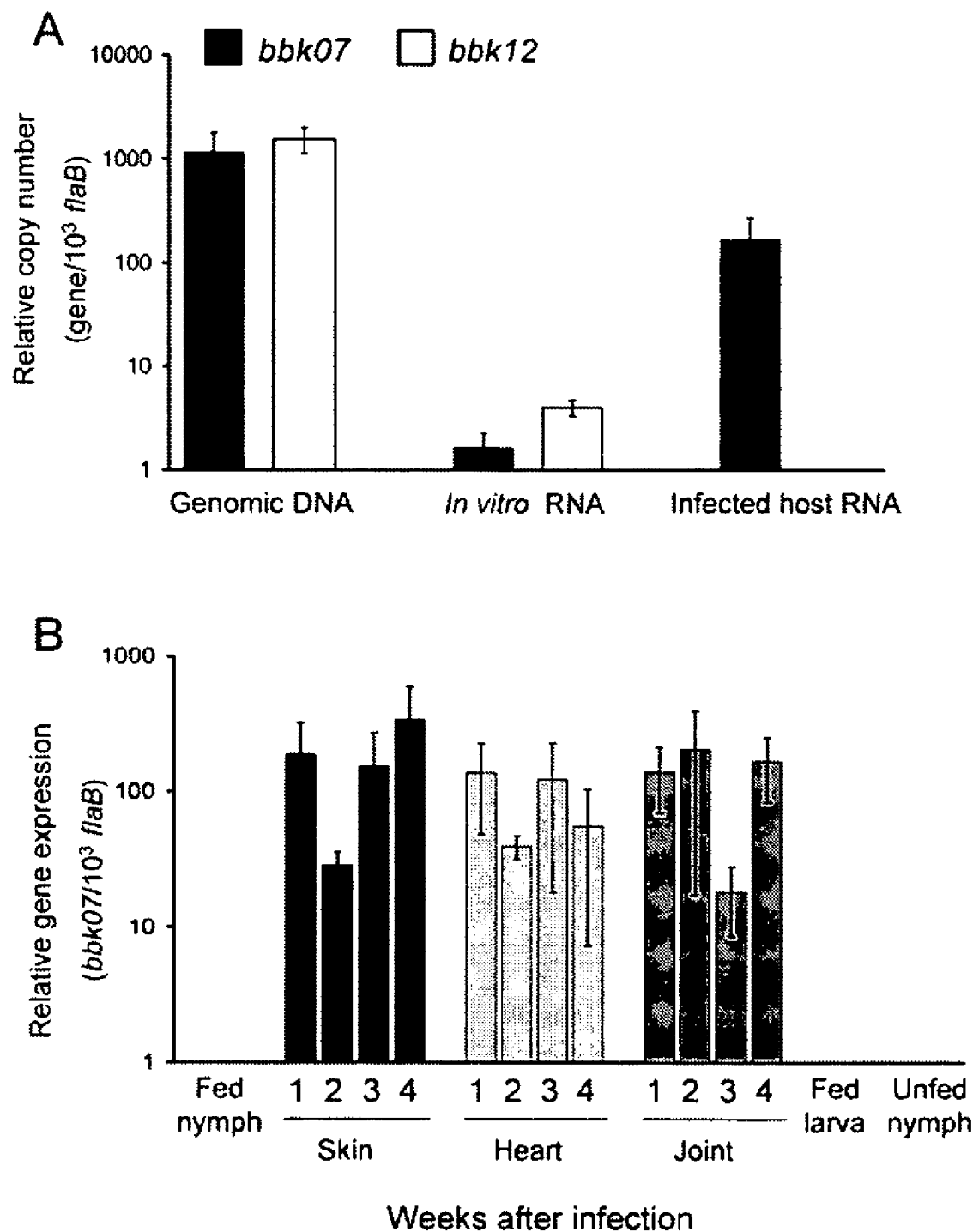
FIG. 1. bbk07 is selectively expressed during infection. (A) bbk07 and bbk12 expression by *B. burgdorferi*. qRT-PCR was performed using gene-specific primers to determine if bbk07, bbk12, or both are transcribed by *B. burgdorferi* in vivo and in vitro, normalized to flaB. Both gene transcripts were detectable at relatively low levels in vitro, but only bbk07 transcripts were present in infected murine skin samples 1 week after inoculation.

BBK07, but not the paralogous gene bbk12, is selectively expressed in the mammal during the infection cycle of *B. burgdorferi*. The paralogous gene products bbk07 and bbk12 have recently been identified as potential immunogens of *B. burgdorferi* (Barbour, A. G. et al., 2008, Infect. Immun. 76, 3374-3389). The genes are highly homologous, with 87% amino acid identity in their overlapping sequences (Fraser, C. M. et al., 1997, Nature 390. 580-265). Due to the nearly identical sequences of BBK07 and BBK12, it is unclear if the host immune response is directed against either or both genes. To ascertain their individual expression patterns, we developed two sets of oligonucleotide primer pairs targeting variable regions of each gene, which specifically amplified either bbk07 or bbk12 with low cross-reactivity, as confirmed by the DNA sequencing of the corresponding amplicons (data not shown). These primers were then used to determine the relative expression levels of each gene in cultured spirochetes or infected host tissue by qRT-PCR analysis. While both genes were transcribed at relatively low levels in vitro, only bbk07 was detectable in vivo, as shown in infected mouse dermis 1 week after inoculation (FIG. 1A). Strikingly, the transcriptional level of bbk07 is more than 100 fold higher in the 16 infected host tissue than in vitro.

Because of the relatively high transcription level of bbk07 in the infected host tissue, we then studied the expression of bbk07 in the *B. burgdorferi* life cycle, covering the first 4 weeks of murine infection. Total RNA was isolated from experimentally infected tick and mouse tissues to generate cDNA representative of important stages in the *B. burgdorferi* life cycle: transmission from infected ticks, murine infection, acquisition by naive ticks, and persistence through the tick molt. While consistently expressed in multiple murine tissues during the first 4 weeks of murine infection, the transcription of bbk07 was dramatically reduced below the limit of detection in all tested stages of ticks (FIG. 1B). The same RNA samples did not contain detectable quantities of bbk12 transcripts at any tissues or time point examined (data not shown).

Example 3

Amino-terminal region of BBK07 is surface exposed and immunogenic. Since BBK07 is annotated as a lipoprotein, which might be exposed on the spirochete surface, we next assessed the surface localization of BBK07. Expressing a full-length or truncated protein representing carboxy-terminal half of BBK07 proved difficult in *Escherichia coli*, however, an amino-terminal fragment could be purified in sufficient quantities and used for further experimentation. This fragment contained the amino terminus through the first half of the mature protein, referred as BBK07N (FIG. 2A, upper panel). Specific antiserum was generated by immunizing mice with BBK07N and adjuvant. In agreement with a previous study showing the immunogenicity of in vitro translated BBK07 (Barbour et al, 2008, supra), BBK07N also evoked a robust immune response and BBK07N anti-serum recognized both purified BBK07N and native BBK07 from *B. burgdorferi* lysate (FIG. 2A, lower panel).

To test the surface exposure of BBK07, a proteinase K accessibility assay was performed (Coleman, A. S. et al., 2008, supra). Intact *B. burgdorferi* were incubated with and without proteinase K, and probed with FlaB, OspA or BBK07N antiseaim. FlaB, a known subsurface protein, was not degraded, but both the surface protein OspA and BBK07 were significantly degraded, suggesting that the amino terminal region of BBK07 is surface exposed (FIG. 2B).

Example 4

BBK07-specific response is pronounced during active borrelial infection but absent in hosts immunized with lysed pathogens. Because qRT-PCR analysis indicated a dramatic induction of bbk07 in vivo during early infection, we next assessed kinetics of BBK07 antibody development in the host over the first nine weeks of *B. burgdorferi* infection. As qRT-PCR analysis indicated minor expression of bbk07 in vitro, we also assessed, in parallel, BBK07 antibody development in mice immunized with sonicated spirochetes, in order to test whether BBK07 could differentiate infected hosts from one vaccinated with killed pathogens. To accomplish this, groups of mice (5 animals/group) were needle-inoculated with a single *B. burgdorferi* inoculum ($10^6$ cells/mice). In parallel, another group of mice (5 animals/group) were injected with sonicated *B. burgdorferi* (100 ug/mouse) at 7 days intervals for a total of 9 weeks. Serum samples were collected and pooled weekly. Equal amounts of *B. burgdorferi* lysate or BBK07N were used to detect specific antibodies present in each serum sample by ELISA (FIG. 3A). As a negative control, antibody development against the *B. burgdorferi* antigen Lp6.6, which is abundant in vitro but known to be downregulated during murine infection, was also measured (Lahdenne, P. et al., 1997, Infect. Immun. 65, 412-421). As expected, antibodies against *B. burgdorferi* lysate, but not against Lp6.6 were detected in infected mice (Brooks, C. S. et al., 2003, Infect. Immun. 71, 3371-3383; Lahdenne, P. et al., 1997, supra). BBK07 provoked a robust antibody development that was detectable after one week, and remained elevated throughout the infection.

Example 5

Evaluation of BBK07N as a diagnostic marker for *B. burgdorferi* infection in murine hosts. The robust and specific immune response provoked by BBK07 led us to investigate a possible diagnostic use of BBK07N. Using mouse serum collected 2 weeks after infection, we compared the immunogenicity of BBK07N to several other immunogenic *B. burgdorferi* antigens, such as VlsE, OspC, BmpA and BbCRASP-2. As controls, *B. burgdorferi* lysate and Lp6.6 were also included in the assay. To measure the relative immunogenicity of each antigen, equal amounts of proteins and lysate were used in an ELISA, probed with the infected mouse serum (FIG. 4). Due to the high antibody titers detected by BBK07N and VlsE, which quickly reached upper detection limit of the assay, the reaction was stopped shortly (1 minute) after the addition of chromogenic substrate. As expected, naive sera had low reactivity to all antigens. Amongst all antigens tested, BBK07N reflected the most robust immune response, proving more sensitive than several antigens currently used in LD diagnosis.

Example 6

Detection of BBK07N-specific antibody response in human patients. To further investigate a diagnostic use of BBK07N, human sera from patients diagnosed with LD and normal human sera were used in an ELISA. Wells were coated with recombinant BBK07N, BmpA, OspC, ox *B. burgdorferi* lysate, and probed with human serum followed by the detection antibody. We did not have enough recombinant VlsE in our possession and therefore, VlsE was excluded from the assay. The panel of control sera was used to define the cutoff value for each antigen, representing the $95^{th}$ percentile absorbance value. Samples with an absorbance higher than the cutoff value were considered positive. *B. burgdorferi* lysate displayed the highest sensitivity of the antigens tested, but had the highest cutoff value due to low specificity. Due to its higher specificity, the recombinant antigen BBK07N (12 out of 35 total samples, 34%) was of comparable diagnostic accuracy to that of *B. burgdorferi* lysate (15 out of 35, 43%) when detecting an antibody response in the infected sera (FIG. 5). In contrast, lower sensitivities were observed using BmpA (7 out of 35, 20%) and OspC (3 out of 35, 9%). These data suggest that BBK07N could be developed into a diagnostic tool for evaluating human Lyme disease patients.

Discussion

The identification and characterization of in vivo antigens of S. burgdorferi is central to the improvement of current laboratory diagnostics for LD. A previous study identified BBK07 and BBK12 as novel immunogenic antigens of *B. burgdorferi* (Barbour et al., 2008, supra). We further extend the observation and establish that bbk07, but not highly similar paralogous member bbk12, was expressed at relatively high levels in vivo. We show that a recombinant protein representing the amino-terminal region of BBK07 was able to provoke a specific antibody response against the native protein, providing antibodies that were then used to demonstrate the surface exposure of specific antibody response to active infection with *B. burgdorferi*. As bbk07 had negligible expression in vitro, we show that this antigen could be useful in discriminating antibody development during active infection versus hosts vaccinated with killed pathogen preparations. The detected antibody response during infection was more robust than that detected by several currently used serodiagnostic antigens (Aguero-Rosenfeld, M. E. et al., 2005, Clin. Microbiol., Rev. 18, 484-509; Bacon, R. M. et al., 2003, J. Infect. Dis. 187, 1187-1199). Finally, using a human serum panel with diagnosed LD, we show that BBK07 is a possible marker for the laboratory diagnosis of LD.

Because of the low numbers of *B. burgdorferi* cells present during disease, diagnosis of LD has principally relied on immunological methods (Aguero-Rosenfeld, M. E. et al., 2005, supra). Serodiagnosis is more sensitive than direct detection, but current serodiagnosis methodologies have been responsible for incidences under- and overdiagnosis (Brown, C. S. et al., 2006, Infect. Immun. 74, 296-304; Ettestad, P. J. et al., 1995, J. Infect. Dis. 171, 356-361; Patel, J. et al, 2003, Clin. Infect. Dis. 31, 1107-1109; Steere, A. C. et al., 1993, J. Am. Med. Assoc. 269, 1812-1816; Tugwell, P. et al., 1997, Ann. Intern. Med. 127, 1109-1123). False negatives can result from tests with low sensitivity, and test sensitivity can be improved by increasing the number of immunoreactive antigens tested. Because *B. burgdorferi* can be grown in vitro, many tests include whole *B. burgdorferi* cells or lysate, which provides an extensive set of antigens (Aguero-Rosenfeld et al., 2005, supra). However, the sensitivity gained by using cultured cells comes with a price, as some antigens of *B. burgdorferi* are conserved amongst other bacterial pathogens (Dressler, F. et al., 1993, J. Infect. Dis. 167, 392-400; Ma, B. et al., 1992, J. Clin. Microbiol. 30, 370-376). Antibodies against conserved antigens such as flagellin and bacterial heat shock proteins are naturally present in many uninfected individuals, increasing the chance of a false positive result (Barbour, A. G. et al., 1986, Infect. Immun. 52, 549-554; Dressler, F. et al., 1993, supra; Hansen, K. et al., 1988, Infect. Immun. 56, 2047-2053; Ma, B. et al., 1992, supra). Perhaps most importantly, the use of *B. burgdorferi* cells makes standardization of the tests more difficult, and as a result, the outcome of tests more subjective. For example, *B. burgdorferi* antigen expression can vary by growth phase, and extended periods of in vitro culture can cause the loss of plasmids, some of which contain important antigens (Purser, J. E. et al., 2000, Proc. Natl. Acad. Sci. U.S.A. 97, 13865-13870; Ramamoorthy, R. and M. T. Philipp, 1998, Infect. Immun. 66, 5119-5124). While in vitro grown *B. burgdorferi* cells may increase sensitivity by providing a wide array of antigens to detect an immune response, the decreased diagnostic specificity and standardization limit its effectiveness in serodiagnosis.

The use of recombinant proteins in diagnosis can eliminate cross-reactive epitopes, and can ease standardization by reducing batch-to-batch variation. This increase in specificity need not come at the cost of sensitivity if the immunodominant antigens of *B. burgdorferi* are identified and characterized. Our data completely support a previous study showing that BBK07 highly immunogenic during LD (Barbour et al, 2008, supra). However, plasmid 1p36. which contained bbk07 locus could be lost during in vitro growth (Jewett, M. W. et al., 2007, Mol. Microbiol. 64, 1357-1374), and our data showing extremely low in vitro expression of bbk07, suggest that bbk07 is under-represented in tests using in vitro grown *B. burgdorferi* (Barbour et al., 2008, supra). The inclusion of BBK07 as a diagnostic marker could increase serodiagnostic sensitivity in human patients while maintaining the high specificity afforded by recombinant antigen tests. The low in vitro expression of bbk07 and undetectable immune response against sonicated borrelial cells suggests additional use of BBK07 in animal LD diagnosis. An animal LD vaccine is commercially available that utilizes killed in vitro grown *B. burgdorferi* (Chu, H. J. et al., 1992, J. Am. Vet. Med. Assoc. 201, 403-411; LaFleur, R. L. et al., 2009, Clin. Vaccine Immunol. 16, 253-259). The presence of BBK07 antibodies could serve as an indicator of active infection, as BBK07 reactivity is unlikely in vaccinated animals immunized with cultured organisms (Gauthier, D. T. and L. S. Mansfield, 1999, J. Vet. Diagn. Invest. 11, 259-265). Thus, BBK07 could differentiate between infected and vaccinated animals. Sequence analysis also indicates that *Borrelia garinii* and *Borrelia afzelii*, the most prevalent causative agents of LD in Europe and Asia, lack an ortholog to BBK07 therefore, BBK07 reactivity could be used to discriminate human LD caused by *B. burgdorferi* from that caused by other strains. bbk07 sequence is highly conserved in major infectious isolates of *B. burgdorferi* (Barbour et al., 2008, supra). Accordingly, BBK07 antibody generated using the infectious B31 isolate used in the current study, also recognized the native protein in infectious *B. burgdorferi* isolate 297, a human cerebrospinal fluid isolate (Steere, A. C. et al., 1977, Arthritis Rheum 20, 7-17), without detectable cross-reactivity (data not shown).

When compared to the robust BBK07-specific antibody development in our murine 14 experiments, the reactivity of the human serum against BBK07 was relatively lower. The lower specific antibody titers in these sera could be the result of a number of factors, including long-term storage of the sera. However, when compared to the human antibody response against *B. burgdorferi* lysate, BBK07 antigen was sensitive enough to detect specific antibodies in many patients, with a diagnostic accuracy similar to that of the lysate. Taken together, current results highlight BBK07 as a promising antigenic marker of LD, and suggest its inclusion as a serodiagnostic agent in order to improve the sensitivity of current laboratory testing.

Example 7

BBK07 immunodominant epitopes. We further sought to identify the immunodominant epitopes of BBK07 in our effort to enhance the sensitivity and specificity of BBK07-based serodiagnosis of LD. A library of 23 overlapping peptides covering the full-length antigen was synthesized to identify the most immunogenic regions of the protein and to develop a BBK07 peptide-based diagnostic kit. An overlapping peptide library based on the predicted BBK07 amino acid sequence was synthesized in order to identify most immunodominant epitopes of the full-length antigen (Table 1).

TABLE 1

Amino acid sequences of overlapping BBK07 peptides Bold face indicated peptides housing most immunodominant epitopes, as assessed by reactivity to patient sera with diagnosed human Lyme disease.

| Peptide name | Sequence | |
|---|---|---|
| P1 | CKWHVDNPIDEATA | (SEQ ID NO: 2) |
| P2 | EATAESKSALTSVD | (SEQ ID NO: 16) |
| P3 | TSVDQVLDEISEAT | (SEQ ID NO: 17) |
| P4 | SEATGLSSEKITKL | (SEQ ID NO: 18) |
| P5 | ITKLTPEELENLAK | (SEQ ID NO: 3) |
| P6 | NLAKEAQDDSEKSK | (SEQ ID NO: 19) |
| P7 | EKSKKEIEDQKNTK | (SEQ ID NO: 4) |
| P8 | KNTKESKNIEVKDT | (SEQ ID NO: 20) |
| P9 | VKDTPRLIKLIKNS | (SEQ ID NO: 21) |
| P10 | IKNSSEKIDSVFQT | (SEQ ID NO: 22) |
| P11 | VFQTLINIGYNATY | (SEQ ID NO: 23) |
| P12 | NATYAAKSNLKNGL | (SEQ ID NO: 24) |
| P13 | KNGLKMVKLLDELL | (SEQ ID NO: 25) |
| P14 | DELLKISVSSNGDK | (SEQ ID NO: 26) |

TABLE 1-continued

Amino acid sequences of overlapping BBK07 peptides Bold face indicated peptides housing most immunodominant epitopes, as assessed by reactivity to patient sera with diagnosed human Lyme disease.

| Peptide name | Sequence | |
|---|---|---|
| P15 | NGDKSTQKYNELKT | (SEQ ID NO: 27) |
| P16 | ELKTWNRFNAENS | (SEQ ID NO: 28) |
| P17 | AENSAIKVPLENGS | (SEQ ID NO: 29) |
| P18 | ENGSKIEAKKCIKT | (SEQ ID NO: 30) |
| P19 | CIKTLMTNVETYFK | (SEQ ID NO: 31) |
| P20 | TYFKGVSTELKDKK | (SEQ ID NO: 32) |
| P21 | KDKKDDKYTKILAA | (SEQ ID NO: 33) |
| P22 | ILAALSEAANKIEN | (SEQ ID NO: 34) |
| P23 | KIENAAMAIHLCFNN | (SEQ ID NO: 35) |

Each peptide was tested for ELISA reactivity in serum samples from healthy donors or patients diagnosed with LD. All peptides were biotinylated at the N-terminus, and experiments using streptavidin-coated plates did not significantly change the results observed (data not shown). Therefore, all subsequent studies used the peptides that were coated directly on ELISA plates. The mean OD value of the control sera (plus 3 SD) was considered the cutoff value to determine positivity in the sample from patients diagnosed with LD. The results show that most immunodominant epitopes of BBK07 are concentrated in the amino-terminal region of the protein with Peptide no. 1-C K W H V D N P I D E A T A (SEQ ID NO:2), Peptide no. 5-I T K L T P E E L E N L A K (SEQ ID NO:3) and Peptide no. 7-E K S K K E I E D Q K N T K (SEQ ID NO:4) being most immunogenic in serum collected from human LD patients (FIG. 6A, Table 1). Given the number of peptides and the limited supply of serum, all peptides were screened once with each serum sample, and the most immunogenic peptides were repeated to validate the results. Peptides P1, P5, and P7 were retested twice against all sera, for a total of 3 independent measurements. Samples were considered positive if they exceeded the cutoff value in at least 2 out of 3 assays. Repeated measurements confirmed that peptides P1, P5 and P7 contained immunogenic epitopes recognized by the infected sera (FIG. 6B). Individually, P5 housed most immunogenic epitope and was able to distinguish 24% (8 out of 34) of the LD diagnosed patient sera from control. In order to increase the sensitivity of the assay, the three most immunogenic peptides were combined and tested with all sera 3 times as before (FIG. 6B). The synergistic effect of 3 peptides combined together significantly increased the sensitivity of the assay up to 50% (P1+P5+P7, 17 out of 34) (FIG. 6B). The synergistic effect of 3 peptides combined together significantly increased the sensitivity of the assay up to 50% (P1+P5+P7, 17 our of 34 (FIG. 7). Based on the above results, we conclude that the sensitivity of BBK07-based serodiagnosis of human LD is substantially enhanced by the use of a combination of three amino-terminal immunodominant peptides of BBK07.

Overall, this study indicates that a BBK07 peptide-based diagnostic kit is useful for diagnosis of human LD.

What is claimed is:

1. An isolated BBK07 peptide, wherein the peptide is immunoreactive with an antibody against BBK07 of a *Borrelia burgdorferi*, said peptide comprising an amino acid sequence of up to 80 amino acids, said sequence comprising any one of Peptide 1, identified as amino acids 16-29 of SEQ ID NO:1, Peptide 5, identified as amino acids 56-69 of SEQ ID NO:1 or Peptide 7, identified as amino acids 76-89 of SEQ ID NO:1.

2. A composition comprising an isolated BBK07 peptide of claim 1, further comprising one or more additional peptides which are specific for immunoreactive with antibodies against BBK07 or a different protein of the same or a different pathogenic *Borrelia*.

3. The composition of claim 2 wherein said additional peptides are chosen from the group consisting of Peptide 1 identified as amino acids 16-29 of SEQ ID NO:1, Peptide 5 identified as amino acids 56-69 of SEQ ID NO:1, Peptide 7 identified as amino acids 76-89 of SEQ ID NO:1, and BBK07N identified as amino acids 18-142 of SEQ ID NO:1.

4. A kit for detecting Lyme disease in a biological sample from a subject suspected of having Lyme disease, comprising
a composition comprising one or more BBK07 peptide of claim 1 capable of forming an peptide-antibody complex under conditions effective for forming said complex;
a buffer or components necessary for producing a buffer;
means for detecting immune complexes formed between the protein and antibodies present in the sample.

5. The kit of claim 4 wherein said kit further comprises one or more additional peptides which are immunoreactive with antibodies against BBK07 or a different protein of the same or a different pathogenic *Borrelia*.

6. The kit of claim 5 wherein said additional peptides are chosen from the group consisting of Peptide 1 identified as amino acids 16-29 of SEQ ID NO:1, Peptide 5 identified as amino acids 56-69 of SEQ ID NO:1, Peptide 7 identified as amino acids 76-89 of SEQ ID NO:1, and BBK07N identified as amino acids 18-142 of SEQ ID NO:1.

7. The peptide of claim 1 wherein said peptide is modified by one or more modification chosen from the group consisting of: glycosylation, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma carboxylation, glycosylation, GPI anchor formation, hydroxylation, ADP-ribosylation, iodination, methylation, myristoylation, oxidation, proteolytic processing, phosphorylation, prenylation, racemization, selenoylation, sulfation, ubiquitination, modifications with fatty acids, transfer-RNA mediated addition of amino acids to proteins by arginylation, denaturation with heat, denaturation with SDS, and modification to provide an additional N- or C-terminal amino acid sequence suitable for biotinylation or suitable for chemical lipidation.

8. The peptide of claim 1 wherein said peptide is associated with one or more moieties chosen from the group consisting of: a detectable label, a fusion partner, or a substrate that immobilizes the peptide.

9. The peptide of claim 8 wherein said association is covalent or non-covalent, is by a chemical coupling agent, or via a terminal amino acid linker, wherein the linker is either Lysine or Cysteine.

10. The peptide of claim 8 wherein said substrate is a microwell plate, an immobilon, a nitrocellulose membrane, or latex beads.

11. The peptide of claim 8 wherein said fusion partner is a chemical compound or a peptide.

12. The peptide of claim 11 wherein said chemical compound fusion partner is polyethylene glycol.

13. The peptide of claim 11 wherein said peptide fusion partner is beta-galactosidase, glutathione-S-transferase, or a histidine tag.

14. The peptide of claim 1 in a combination with one or more additional peptides or polypeptides from BBK07 or from a non-BBK07 protein from the same or a different pathogenic *Borrelia* strain.

15. The peptide of claim 14 wherein said additional BBK07 peptides are chosen from the group consisting of Peptide 1 identified as amino acids 16-29 of SEQ ID NO:1, Peptide 5 identified as amino acids 56-69 of SEQ ID NO:1, and Peptide 7 identified as amino acids 76-89 of SEQ ID NO:1, BBK07N identified as amino acids 18-142 of SEQ ID NO:1.

16. The peptide of claim 14 wherein the additional peptide(s) or polypeptide(s) also bind specifically to an antibody against a pathogenic *Borrelia*.

17. The peptide of claim 14 wherein the combination comprises a cocktail of individual peptides or polypeptide.

18. The peptide of claim 14 wherein the combination comprises a fusion peptide or polypeptide or a multimeric peptide.

19. The peptide of claim 14 wherein additional peptide(s) contain B-cell and/or T-cell epitopes from a protein of a pathogenic *Borrelia*.

20. The peptide of claim 14 wherein the additional peptides or polypeptides are obtained from *Borrelia* antigens OspA, OspB, DbpA, flagella-associated proteins FlaA(p37), FlaB (p41), OspC (25 kd), BBK32, BmpA(p39), p21, p39, p66 or p83.

21. The peptide of claim 14 wherein the additional peptides are derived from microorganisms other than *Borrelia*.

22. The peptide of claim 1 wherein said peptide is linked at the N-terminal or at the C-terminal to another non-BBK07 peptide or polypeptide.

23. The peptide of claim 22 wherein said linking is through one or more spacers.

24. An isolated polypeptide of up to 80 amino acids comprising Peptide 1, identified as amino acids 16-29 of SEQ ID NO:1, Peptide 5, identified as amino acids 56-69 of SEQ ID NO:1, and Peptide 7, identified as amino acids 76-89 of SEQ ID NO:1 wherein the peptides are fused or linked.

25. A method for detecting Lyme disease in a biological sample from a subject suspected of having Lyme disease, comprising
  (i) contacting said biological sample with a composition comprising one or more BBK07 peptide of claim 1 capable of forming an peptide-antibody complex under conditions effective for forming said complex, wherein said peptide is labeled with a detectable label; and
  (ii) detecting the presence of said complexes visually or mechanically.

26. The method of claim 25, wherein the detecting is performed with an ELISA assay.

27. The composition of claim 2 further comprising BBK07N identified as amino acid 18-142 of SEQ ID NO:1.

28. A method for discriminating human Lyme disease caused by *B. burgdorferi* and that caused by other *Borrelia* strains, said method comprising detecting the presence of an antibody to the BBK07 peptide of claim 3 in a sample from said human, wherein the presence of the antibody to BBK07 peptide indicates a *B. burgdorferi* infection and absence of a BBK07 peptide indicates infection is *Borrelia* other than *B. burgdorferi*.

* * * * *